US012091423B2

(12) United States Patent
Ivachtchenko et al.

(10) Patent No.: US 12,091,423 B2
(45) Date of Patent: Sep. 17, 2024

(54) SUBSTITUTED 3,4,12,12A- TETRAHYDRO-1H-[1,4]OXAZINO[3,4-C]PYRIDO[2,1-F][1,2,4] TRIAZINE-6,8-DIONE, PHARMACEUTICAL COMPOSITION, METHOD FOR THE PRODUCTION AND USE THEREOF

(71) Applicant: VIRIOM, INC., San Diego, CA (US)

(72) Inventors: Alexandre Vasilievich Ivachtchenko, Hallandale, FL (US); Andrey Alexandrovich Ivashchenko, Moscow (RU); Oleg Dmitrievich Mitkin, Khimki (RU)

(73) Assignee: VIRIOM, INC., San Diego, CA (US)

( * ) Notice: Subject to any disclaimer, the term of this patent is extended or adjusted under 35 U.S.C. 154(b) by 0 days.

(21) Appl. No.: 16/768,892

(22) PCT Filed: Mar. 27, 2020

(86) PCT No.: PCT/RU2020/000163
§ 371 (c)(1),
(2) Date: Jun. 2, 2020

(87) PCT Pub. No.: WO2020/226532
PCT Pub. Date: Nov. 12, 2020

(65) Prior Publication Data

US 2022/0048925 A1 Feb. 17, 2022

(30) Foreign Application Priority Data

May 7, 2019 (RU) ........................... RU2019113751

(51) Int. Cl.
*C07D 498/14* (2006.01)
*A61K 31/5383* (2006.01)
*A61P 31/16* (2006.01)

(52) U.S. Cl.
CPC ........ *C07D 498/14* (2013.01); *A61K 31/5383* (2013.01); *A61P 31/16* (2018.01)

(58) Field of Classification Search
CPC .... C07D 498/14; A61P 31/16; A61K 31/5383
See application file for complete search history.

(56) References Cited

U.S. PATENT DOCUMENTS 9,827,244 B2 11/2017 Schulz-Gasch et al.
2020/0283454 A1* 9/2020 Tang .................... C07D 519/00

FOREIGN PATENT DOCUMENTS

| | | |
|---|---|---|
| RU | 2608519 | 1/2017 |
| RU | 2019113751 | 4/2020 |
| WO | WO 2016175224 | 11/2016 |
| WO | WO 2018030463 | 2/2018 |

OTHER PUBLICATIONS

RN2303912-72-1 (Year: 2019).*

* cited by examiner

*Primary Examiner* — Jeffrey S Lundgren
*Assistant Examiner* — Ibrahim D Bori
(74) *Attorney, Agent, or Firm* — Paul D. Strain, Esq.; Strain & Strain PLLC

(57) ABSTRACT

Influenza is an acute infectious respiratory disease caused by the influenza virus. It is part of the group of Acute Respiratory Viral Infections (ARVI). It occasionally spreads in the form of epidemics and pandemics. Currently, more than 2000 variants of the influenza virus differing in the antigen spectrum have been identified. Given that influenza is a serious threat to public health (worldwide, these annual epidemics lead to 3-5 million cases of severe illness, millions of hospitalizations, and up to 650,000 deaths), it seems appropriate to search for new anti-influenza drugs with improved characteristics.

Figure 1:
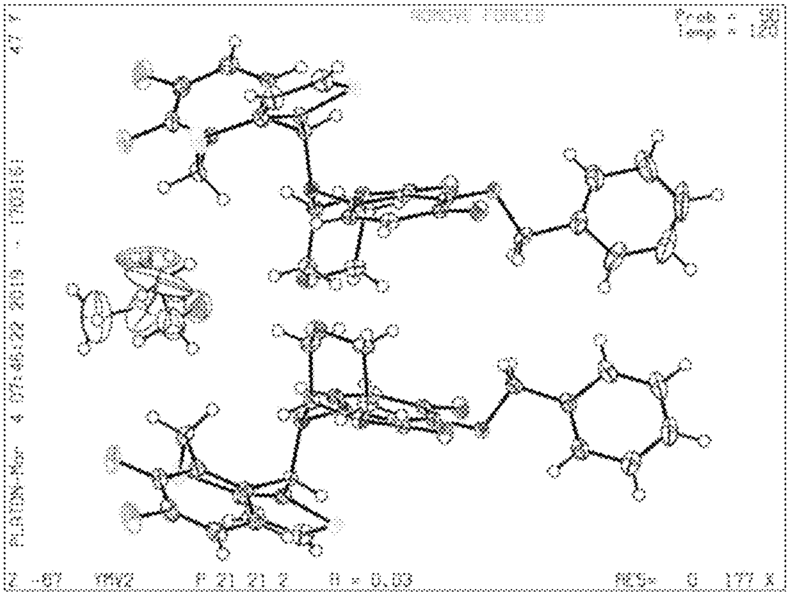
Figure 1:
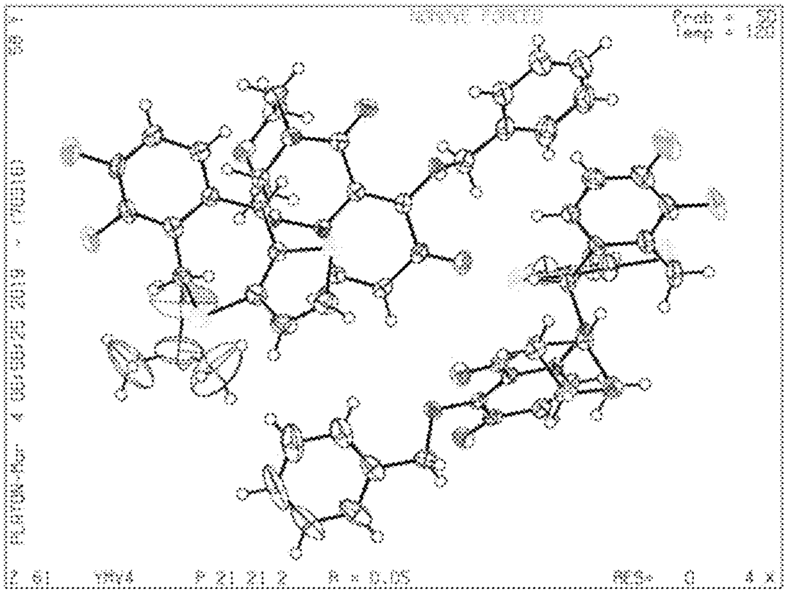

The inventors surprisingly found out that the previously unknown substituted 3,4,12,12a-tetrahydro-1H-[1,4] oxazino[3,4-c]pyrido[2,1-f] [1,2,4]triazine-6,8-dione of general formula 1, its stereoisomer, their prodrug, pharmaceutically acceptable salt, solvate, hydrate, and a crystalline or polycrystalline form thereof are effective agents for prophylaxis and treatment of viral diseases, including influenza

1

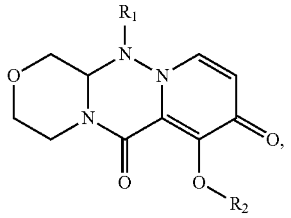

where $R^1$ is (6,7-difluoro-5,10-dihydrothieno[3,2-c][2]benzothiepin-10-yl, (7,8-difluoro-4,9-dihydrothieno[2,23-c][2]benzothiepin-4-yl, (3,4-difluorophenyl)(phenyl)methyl, (3,4-difluorophenyl)(2-methylsulfanylphenyl)methyl, diphenylmethyl, bis(4-fluorophenyl)-methyl; $R^2$ is hydrogen or a protective group selected from a series comprising (C1-C3 alkyl) oxycarbonyloxy, {[(C1-C3 alkyl)oxycarbonyl]-oxy}methoxy, {[2-(C1-C3 alkyl) oxyethoxy]carbonyl}oxy, ({[(1R)-2-[(C1-C3alkyl)oxy]-1-methylethoxy} carbonyl) oxy, {[(3S)-ethoxyfuran-3-yloxy]-carbonyl}oxy, [(ethoxy-2H-pyran-4-yloxy) carbonyl]oxy, {[(1-acetylazetidine)-3-yloxy]carbonyl}oxy, {[(C1-C3alkyl) oxycarbonyl]-oxy} methoxy, ({[2-(C1-C3 alkyl)oxyethoxy]carbonyl}oxy) methoxy.

4 Claims, 3 Drawing Sheets

A

B

A

B

SUBSTITUTED 3,4,12,12A- TETRAHYDRO-1H-[1,4]OXAZINO[3,4-C]PYRIDO[2,1-F][1,2,4]TRIAZINE-6,8-DIONE, PHARMACEUTICAL COMPOSITION, METHOD FOR THE PRODUCTION AND USE THEREOF

CROSS-REFERENCE TO RELATED PATENT APPLICATIONS

This application is a National Stage of International Application No. PCT/RU2020/000163, filed Mar. 27, 2020, which is based upon and claims the benefit of priority from prior Russian Patent Application No. 2019113751, filed May 7, 2019, the entire contents of all of which are incorporated herein by reference in their entirety.

FIELD OF THE INVENTION

The present invention relates to a novel compound substituted 3,4,12,12a-tetrahydro-1H-[1,4] oxazino[3,4-c] pyrido[2,1-f] [1,2,4]triazine-6,8-dione, which is an effective tool for the prevention and treatment of viral diseases, including influenza.

BACKGROUND OF THE INVENTION

Influenza is an acute infectious respiratory disease caused by the influenza virus. It is part of the group of acute respiratory viral infections (ARVI). It occasionally spreads in the form of epidemics and pandemics. Currently, more than 2000 variants of the influenza virus have been identified, which differ in the antigen spectrum. According to WHO estimates, every year from 250 to 500 thousand people (most of them older than 65 years) die in the world from all variants of the virus during seasonal epidemics, and in some years the number of deaths can reach a million.

The virus was first isolated in the 1930s. Influenza viruses belong to the family of Orthomyxoviruses (Latin: Orthomyxoviridae), a family of RNA-containing viruses. This family includes seven types of viruses, including influenza A virus, influenza B virus, influenza C virus, and influenza D virus. Three types of influenza virus that are identified by antigenic differences in their nucleoprotein and matrix protein infect vertebrates as follows: influenza A virus infects humans, other mammals, and birds and causes all influenza pandemics. Influenza B virus infects humans and seals. Influenza C virus infects humans, pigs, and dogs. Influenza D virus (isolated in 2012) infects farm animals. As far as we know, influenza D does not infect human cells.

Viruses containing three subtypes of hemagglutinin (HA) surface proteins (H1, H2, H3) and two subtypes of neuraminidase (NA) (N1, N2) have epidemic significance for humans. Influenza viruses A and B contain NA and NA as the main structural and antigenic components of the viral particle, which have hemagglutinating and neuraminidase activities. The influenza C virus does not have neuraminidase, but instead has a hemagglutinin-esterase (penetrating) protein (HEF).

A significant achievement in modern biology and medicine is the development and introduction into practice of methods for the treatment of viral infections aimed at eliminating the cause of the disease and based on the use of specific inhibitors that block the functional activity of the virus at different stages of its replication cycle.

Most anti-influenza drugs currently on the market are inhibitors of neuraminidase (zanamivir, oseltamivir, peramivir) or the M2 protein that forms proton ion channels (amantadine, rimantadine) [Hayden, F. G. Antivirals for influenza: historical perspectives and lessons learned. Antiviral Res 71, 372-8 (2006).]. However, these targets, especially the latter, are susceptible to rapid mutations that can confer antiviral resistance due to the inability of viral RNA-dependent RNA polymerase (RdRp) to correct RNA during replication. In fact, the World Health Organization's Global Influenza Program reported that >99% of seasonal influenza A strains are now resistant to amantadine and rimantadine [Barr, I. G. et al. WHO recommendations for the viruses used in the 2013-2014 Northern Hemisphere influenza vaccine: Epidemiology, antigenic and genetic characteristics of influenza A (H1N1) pdm09, A (H3N2) and influenza B viruses collected from October 2012 to January 2013. Vaccine 32, 4713-25 (2014).]. This has led to the search for new antiviral compounds targeting at other important viral processes [Yen, H. L. Current and novel antiviral strategies for influenza infection. Curr Opin Virol 18, 126-134 (2016).]. In this connection, RNA-dependent RNA polymerase (RdRp) or RNA replicase of the influenza virus is itself an attractive drug target, since it develops drug resistance relatively slowly, persists in genotypes, and is important for virus replication.

In the last decade, the understanding of influenza virus RdRp has dramatically expanded through the elucidation of the high-resolution architecture of influenza endonuclease [Dias, A. et al. The cap-snatching endonuclease of influenza virus polymerase resides in the PA subunit. *Nature* 2009, 458, 914-918. Pflug, A. et al. Structure of influenza A polymerase bound to the viral RNA promoter. *Nature* 2014, 516, 355-360.] and the discovery of a complete heterotrimeric RdRp structure [Hengrung, N. et al. Crystal structure of the RNA-dependent RNA polymerase from influenza C virus. *Nature* 2015, 527, 114-117.].

Located in the nuclei of infected cells, the influenza virus RdRp is represented by a heterotrimer consisting of three subunits: PA, PB1 and PB2. RdRp is responsible for replication and transcription of eight different RNA segments of the viral genome. This viral polymerase synthesizes viral mRNAs using short cap primers of the host cell. These cap primers are derived from cellular transcripts (RNA) using a unique cap-dependent mechanism. In an infected cell, the PB2 viral subunit binds the pre-mRNA cap at their 5' ends. Then, these cap-RNAs bound with the PB2 subunit are cleaved by viral endonuclease after 10-13 nucleotides. Biochemical and structural studies have shown that the endonuclease active center is located at the amino-terminal site of 209 amino acid residues of the PA subunit. This domain has endogenous RNA and DNA endonuclease activity that is strongly activated by manganese ions. This corresponds to observations that reported dependence of the endonuclease activity of an intact three-subunit polymerase on manganese [Dias, A. et al., 2009]. The possibility of inhibiting this endonuclease activity was first established almost a quarter of a century ago on the example of 4-substituted 2,4-dioxobutane acids (for example, compounds A1 and A2) [J. Tomassini et al. Inhibition of cap (m7GpppXm)-dependent endonuclease of influenza virus by 4-Substituted 2,4-dioxobutanoic acid compounds. *Antimicrob. Agents Chemoter.* 1994, 2827-2837].

A1

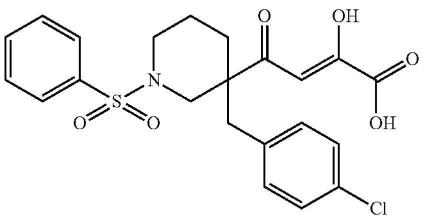

A2

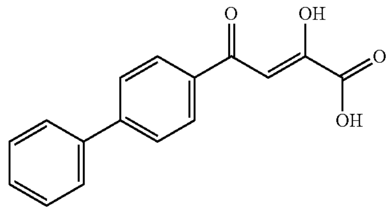

A little later, natural cap-dependent transcriptase inhibitors of the influenza A and B viruses were isolated from the *Delitschia confertaspora* culture as substituted 2,6-diketopiperazines, including Flutimide (A3) [J. Tomassini et al. A Novel Antiviral Agent Which Inhibits the Endonuclease of Influenza Viruses. *Antimicrob. Agents Chemoter.* 1996, 1189-1193], as well as synthetic drugs Favipiravir (A4) [Furuta Y. et al. T-705 (favipiravir) and related compounds: Novel broad-spectrum inhibitors of RNA viral infections. *Antiviral Research.* 2009, 82 (3), 95-102.] and Pimodivir (A5) [Clark, M. P. et al. Discovery of a novel, first-in-class, orally bioavailable azaindole inhibitor (VX-787) of influenza PB2. *J. Med. Chem.* 2014, 57, 6668-6678. Byrn, R. A. et al. Preclinical activity of VX-787, a first-in-class, orally bioavailable inhibitor of the influenza virus polymerase PB2 subunit. *Antimicrob. Agents Chemother.* 2015, 59, 1569-1582. https://ichgcp. net/clinical-trials-registry/NCT02342249].

A3

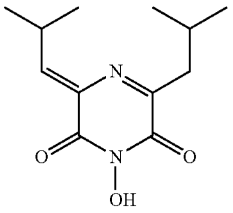

Flutimide

A4

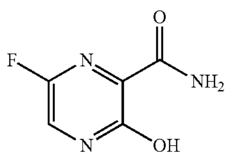

Favipiravir, T-705, Avigan

-continued

A5

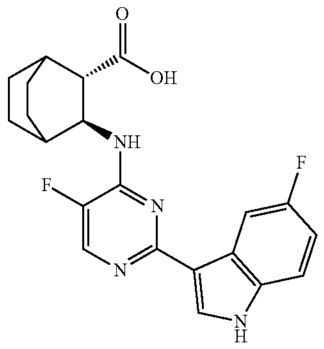

Pimodivir, JNJ-3872, JNJ-872, JNJ-63623872, VX 78

Favipiravir (A4) is a broad-spectrum drug targeted at numerous viral RdRps, including influenza virus. It was approved in Japan in 2014 and in the United States in 2015 for emergency use in the event of an influenza pandemic despite some significant concerns about the drug's toxicity [Nagata, T. et al. Favipiravir: a new medication for the Ebola virus disease pandemic. Disaster Med Public Health Prep 9, 79-81 (2015).].

Pimodivir (A5) is a first-in-class inhibitor of influenza virus replication that blocks PB2 activity of the influenza virus polymerase complex [Clark, M. P. et al. Discovery of a novel, first-in-class, orally bioavailable azaindole inhibitor (VX-787) of influenza PB2. *J. Med. Chem.* 2014, 57, 6668-6678. Byrn, R. A. et al. Preclinical activity of VX-787, a first-in-class, orally bioavailable inhibitor of the influenza virus polymerase PB2 subunit. *Antimicrob. Agents Chemother.* 2015, 59, 1569-1582. https://ichgcp.net/clinical-trials-registry/NCT02342249]. The drug is in phase 3 of a clinical trial to evaluate the efficacy and safety of pimodivir in combination with standard treatment in adolescents, adults, and elderly patients infected with influenza A [https://clinicaltrials.gov/ct2/show/NCT03376321].

Relatively recently, polyheterocyclic cap-dependent endonuclease inhibitors comprising a fragment of substituted 2,4-dioxobutanoic acid have been patented, including inhibitors A6 and A7 [EP 2620436B1 (priority 2010), https://patents.google.com/patent/EP2620436B1], A8, A9 [U.S. Pat. No. 9,827,244B2 (priority 2016)] and A10, A11 [WO 2016175224A1; WO 2018030463 (priority 2016)].

A6

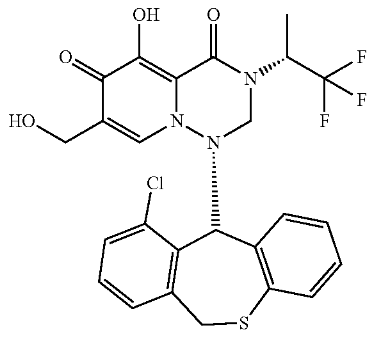

-continued

A7

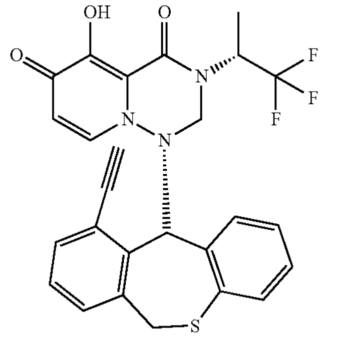

A8

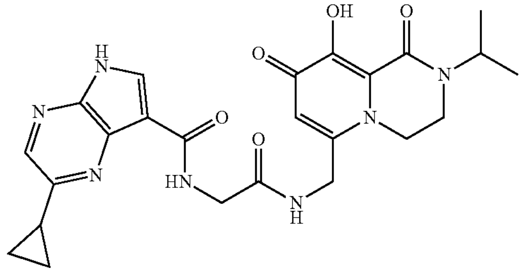

A9

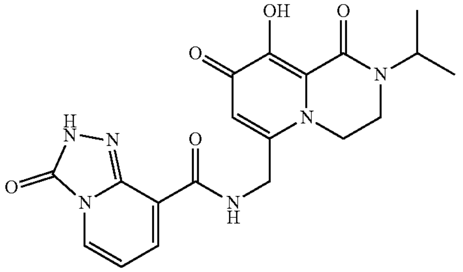

A10

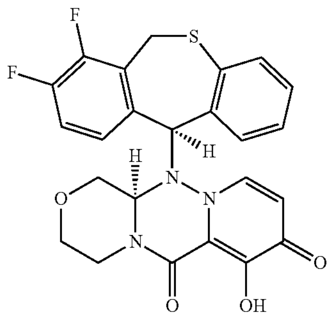

(Baloxavir, Baloxavir acid, BXA)

-continued

A11

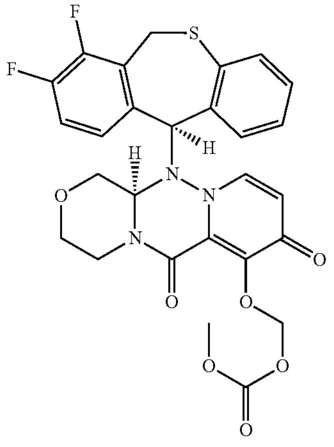

(Baloxavir marboxil, BXM, Xofluza®)

It seems that the most potent drug in this range of inhibitors is Baloxavir A10 (Baloxavir acid, BXA, (12aR)-7-hydroxy-12-[(11S)-5,11-dihydro[1]benzothiepino[3,4-b]pyridin-5-yl]-3,4,12,12a-tetrahydro-1H-[1,4]oxazino[3,4-c]pyrido[2,1-f][1,2,4]triazine-6,8-dione), the prodrug of which named Baloxavir marboxil A11 (BXM, 5-033188) having a trade name of Xofluza® was approved in 2018 in Japan and the United States for treating influenza A and B infections.

Xofluza® is the first in almost 20 years oral antiviral drug with a new mechanism of action for the treatment of influenza [S. Omoto at al. Characterization of influenza virus variants induced by treatment with the endonuclease inhibitor baloxavir marboxil. *Scientific Reports* 2018, 8, Article number: 9633].

Considering the fact that influenza poses a serious threat to public health (on a global scale, annual epidemics lead to 3-5 million cases of severe illness, millions of hospitalizations and up to 650,000 deaths worldwide), it makes sense to search for new anti-influenza drugs with improved characteristics.

The inventors surprisingly found out that the previously unknown substituted 3,4,12,12a-tetrahydro-1H-[1,4]oxazino[3,4-c]pyrido[2,1-f] [1,2,4]triazine-6,8-dione of general formula 1, its stereoisomer, their prodrug, a pharmacologically acceptable salt, solvate, hydrate, and their crystalline or polycrystalline form, including this novel compound, pharmaceutical composition, are effective anti-influenza agents.

1

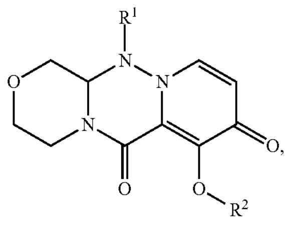

where $R^1$ is 6,7-difluoro-5,10-dihydrothieno[3,2-c][2]benzothiepin-10-yl, 7,8-difluoro-4,9-dihydrothieno[2,23-c][2]benzothiepin-4-yl, (3,4-difluorophenyl)(phenyl)methyl, (3,4-difluorophenyl)(2-methylsulfanylphenyl)methyl, diphenylmethyl, (3,4-difluorophenyl)(2-methylsulfanylphenyl)methyl, diphenylmethyl, bis(4-fluorophenyl)methyl; $R^2$ is hydrogen or a protective group.

Listed below are definitions of various terms used to describe this invention. These definitions apply to the terms as they are used throughout this specification and claims, unless otherwise limited in specific instances, either individually or as part of a larger group.

The term "aryl," as used herein and unless otherwise specified, refers to substituted or non-substituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected or protected as necessary, as known to those skilled in the art, for example, as described in T. W. Greene and P. G. M. Wuts, "Protective Groups in Organic Synthesis," 3rd ed., John Wiley & Sons, 1999.

The term "heteroaryl," as used herein, refers to a mono- or polycyclic aromatic radical having one or more ring atoms selected from S, O and N; and the remaining ring atoms are carbon. Heteroaryl includes, but is not limited to, pyridinyl, pyrazinyl, pyrimidinyl, quinolinyl, isoquinolinyl, benzimidazolyl, benzooxazolyl, or quinoxalinyl.

The term "alkyl" as used herein refers to linear or branched unsaturated hydrocarbon radicals containing from one to six carbon atoms. Examples of $C_1$-$C_6$ alkyl radicals include, but are not limited to, methyl, ethyl, propyl, isopropyl, n-butyl, and tert-butyl.

The term "protective group," as used herein, refers to substituents attached to the oxygen of the alcohol group and generally used to block or protect the functionality of alcohol or any other hydroxy compound, which does not prevent interaction with a compound having different functional groups (in: Greene's Protective Groups in Organic Synthesis. Editor: Peter G. M. Chapter 2, Protection for the Hydroxyl Group, Including 1,2□ and 1,3□Diols. P. 17-471, 2014. https://onlinelibrary.wiley.com/doi/book/10.1002/9781118905074). Protective groups are preferably selected from a series containing ($C_1$-$C_3$ alkyl)oxycarbonyloxy, {[($C_1$-$C_3$ alkyl)oxycarbonyl]-oxy}methoxy, {[2-($C_1$-$C_3$ alkyl)oxyethoxy]carbonyl}oxy, ({[(1R)-2-[($C_1$-$C_3$ alkyl)oxy]-1-methylethoxy]}carbonyl)oxy, {[(3S)-ethoxyfuran-3-yloxy]-carbonyl}oxy, [(ethoxy-2H-pyran-4-yloxy)carbonyl]oxy, {[(1-acetylazetidin)-3-yloxy]carbonyl}oxy, {[($C_1$-$C_3$ alkyl)oxycarbonyl]oxy}methoxy, ({[2-($C_1$-$C_3$ alkyl)oxyethoxy] carbonyl}oxy)methoxy.

The term "prodrug" refers to those compounds of this invention that are chemically or metabolically cleaved to become, by solvolysis or under physiological conditions, an in-vivo pharmaceutically active compound of the invention. Prodrugs often have better solubility, tissue compatibility, delivery, or delayed release in mammals (Bungard, H., Design of products, pp. 7-9, 21-24, Elsevier, Amsterdam 1985). Prodrugs include acid derivatives well known to practitioners in the art, such as, for example, esters prepared by reaction of the parent acidic compound with a suitable alcohol, or amides prepared by reaction of combination of the parent acid compound with a suitable amine. Examples of prodrugs include, but are not limited to, acetate, formate, benzoate or other acylated derivatives of alcohol or amine functional groups within the compounds of the invention.

The term "active ingredient" (drug substance), as used herein, refers to a physiologically active compound of synthetic or other (biotechnological, vegetable, animal, microbicidal, and so on) origin exhibiting a pharmacological activity, which is the active ingredient of a pharmaceutical composition.

The term "medicinal drug," as used herein, refers to a compound (or a mixture of compounds forming a pharmaceutical composition) in tablets, capsules, injections, ointments, or other finished dosage forms intended for the restoration, improvement, or modification of physiological functions in humans and animals as well as for the treatment and prophylaxis of diseases, for diagnostics, anesthesia, contraception, cosmetology, etc.

The term "therapeutic cocktail" refers to a simultaneously administered combination of two or more medicinal drugs that exhibit different mechanisms of pharmacological action and are directed at various biotargets taking part in the pathogenesis of disease.

The term "pharmaceutical composition" refers to a composition comprising a compound of general formula 1 and at least one of the components selected from the group consisting of pharmaceutically acceptable and pharmacologically compatible fillers, solvents, diluents, carriers, excipients, distributing, and sensing agents, delivery agents such as preservatives, stabilizers, fillers, disintegrators, moisteners, emulsifiers, suspending agents, thickeners, sweeteners, flavoring agents, aromatizing agents, antibacterial agents, fungicides, lubricants, and prolonged delivery controllers, the choice and proportions of which depend on the nature and route of administration and dosage. Examples of suitable suspending agents are ethoxylated isostearyl alcohol, polyoxyethylene, sorbitol and sorbitol ether, microcrystalline cellulose, aluminum metahydroxide, bentonite, agar-agar and tragacanth, and mixtures thereof. Protection against microorganisms can be provided using various antibacterial and antifungal agents, such as parabens, chlorobutanol, sorbic acid, and the like. Said composition may also include isotonic agents, such as sugar, sodium chloride, and the like. The sustained action of the composition can be achieved using agents that decelerate the absorption of the active ingredient, for example, aluminum monostearate and gelatin. Examples of suitable carriers, solvents, diluents and delivery agents include water, ethanol, polyalcohols and mixtures thereof, natural oils (such as olive oil), and organic esters (such as ethyl oleate) for injections. Examples of fillers are lactose, milk sugar, sodium citrate, calcium carbonate, calcium phosphate, and the like. Examples of disintegrators and distributors are starch, alginic acid and salts thereof, and silicates. Examples of lubricants are magnesium stearate, sodium lauryl sulfate, talc, and polyethylene glycol of high molecular weight. A pharmaceutical composition for peroral, sublingual, transdermal, intramuscular, intravenous, subcutaneous, and local or rectal administration of the active ingredient, alone or in combination with another active ingredient, may be administered to animals and people in a standard administration form as a mixture with traditional pharmaceutical carriers. Suitable standard administration forms include peroral forms, such as tablets, gelatin capsules, pills, powders, granules, chewing gums, and peroral solutions or suspensions; sublingual and transbuccal administration forms; aerosols; implants; local, transdermal, subcutaneous, intramuscular, intravenous, intranasal, or intraocular forms; and rectal administration forms.

The term "inert filler" as used herein refers to a compound that is used for forming a pharmaceutical composition and is, as a rule, safe, nontoxic, and neither biologically nor otherwise undesirable, and comprises excipients acceptable for veterinary and human pharmaceutical use. Compounds of this invention may be administered individually, but they will be generally administered in a mixture with one or more pharmaceutically acceptable excipients, diluents, or carriers chosen depending on the contemplated route of drug administration and standard pharmaceutical practice.

The term "pharmaceutically acceptable salt" refers to relatively nontoxic, both organic and inorganic salts of acids and bases claimed herein. Said salts can be obtained by in situ synthesis, isolation, or purification of compounds or they can be prepared specially. In particular, basic salts can be specially prepared from a purified free base of a compound claimed herein and a suitable organic or inorganic acid. Examples of salts thus prepared include hydrochlorides hydrobromides, sulfates, bisulfates, phosphates, nitrates, acetates, oxalates, valeriates, oleates, palmitates, stearates, laurates, borates, benzoates, lactates, tosylates, citrates, maleates, fumarates, succinates, tartrates, mesylates, malonates, salicylates, propionates, ethanesulfonates, benzenesulfonates, sulfamates, and the like (a detailed description of the properties of said salts is given in Berge S. M., et al., "Pharmaceutical Salts" J. Pharm. Sci. 1977, 66: 1-19). The salts of the acids claimed herein may be also specially prepared by reaction of a purified acid with a suitable base to produce metal salts and amines. Said metal salts include the salts of sodium, potassium, calcium, barium, zinc, magnesium, lithium, and aluminum, of which sodium and potassium salts are preferable. Suitable inorganic bases used to produce metal salts include sodium hydroxide, carbonate, bicarbonate, and hydride; potassium hydroxide and bicarbonate, lithium hydroxide; calcium hydroxide; magnesium hydroxide; and zinc hydroxide. Organic bases used to produce acid salts as claimed herein include amines and amino acids sufficiently basic to form a stable salt and suitable for medical use (in particular, they must be low-toxic). Said amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane, and the like. Furthermore, salts can be prepared using tetraalkylammonium hydroxides, such as choline, tetramethylammonium, tetraethylammonium, and the like. Amino acids may be selected from basic amino acids: lysine, ornithine, and arginine.

The term "crystalline form" refers to a substance structure wherein the molecules are packed to form a crystal lattice.

The term "polycrystalline form" refers to a polycrystalline substance structure consisting of a plurality of small monocrystals, or crystallites of certain crystalline form.

The term "therapeutically effective amount," as used herein, refers to an amount of a substance, prodrug, or drug needed for alleviating the symptoms of the disease in the subject. The dose of a substance, prodrug, or drug will meet individual demands in each particular case. Said dose may vary in a wide range depending on numerous factors like the severity of the disease to be treated, the age and the general condition of the patient, other medicaments used for the patient's treatment, the mode and route of administration, and the experience of the attending doctor. For oral administration, the daily dose is approximately 0.01-10 g, including all values therebetween, both in monotherapy and/or combination therapy. The preferred daily dose is around 0.1-7 g. As a rule, in order to alleviate or eliminate the virus, a higher loading dose is given at the beginning of treatment with a subsequent reduction of the dose to a level sufficient to prevent an infection outburst.

The term "solvate" refers to a complex or an aggregate formed by one or more molecules of a solute, i.e., a compound of this invention or a pharmaceutically acceptable salt thereof and one or more molecules of a solvent. Said solvates are typically crystalline solids having a fixed solute-solvent molar ratio. Representative solvents include, but are not limited to, water, ethanol, isopropanol, acetic acid, and so on. When the solvent is water, the solvate formed is a hydrate.

The term "subject" refers to a mammal including, but not limited to, cattle, hogs, sheep, chickens, turkeys, buffalos, lamas, ostriches, dogs, cats, and humans; a human subject is most preferable. It is assumed that a subject's treatment may involve the use of any prodrug of general formula 1, its stereomer, isotopically enriched analog, pharmaceutically acceptable salt, hydrate, solvate, and crystalline or polymorphic form or their combinations with another compound, including with an HCV NS5A inhibitor.

SUMMARY

The inventors have surprisingly found that the previously unknown substituted 3,4,12,12a-tetrahydro-1H-[1,4] oxazino[3,4-c]pyrido[2,1-f] [1,2,4]triazine-6,8-dione of general formula 1, its stereoisomer, their prodrug, pharmaceutically acceptable salt, solvate, hydrate, and a crystalline or polycrystalline form thereof, or a pharmaceutical composition comprising this novel compound are effective anti-influenza drugs.

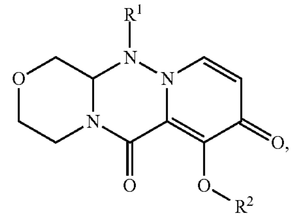

1 where $R^1$ is 6,7-difluoro-5,10-dihydrothieno[3,2-c][2] benzothiepin-10-yl, 7,8-difluoro-4,9-dihydrothieno[2,23-c] [2]benzothiepin-4-yl, (3,4-difluorophenyl) (phenyl)methyl, (3,4-difluorophenyl)(2-methylsulfanylphenyl)methyl, diphenylmethyl, bis(4-fluorophenyl)methyl; $R^2$ is hydrogen or a protective group selected from a series including benzyl (C1-C3 alkyl)oxycarbonyloxy, {[(C1-C3 alkyl)oxycarbonyl]-oxy}methoxy, {[2-(C1-C3 alkyl)oxyethoxy]carbonyl} oxy, ({(1R)-2-[(C1-C3alkyl)oxy]-1-methylethoxy]}carbonyl)oxy, {[(3S)-ethoxyfuran-3-yloxy]-carbonyl}oxy, [(ethoxy-2H-PYRAN-4-yloxy)carbonyl]oxy, {[(1-acetylazetidin)-3-yloxy]carbonyl}oxy, {[(C1-C3 alkyl)oxycarbonyl] oxy}methoxy, ({[2-(C1-C3 alkyl)oxyethoxy]carbonyl}oxy) methoxy.

Preferable compounds are:

(12aR)-12-(6,7-difluoro-5,10-dihydrothieno[3,2-c][2]benzothiepin-10-yl)-3,4,12,12a-tetrahydro-1H-[1,4]oxazino [3,4-c]pyrido[2,1-f][1,2,4]triazine-6,8-dione of general formula 1.1, (12aR)-12-[(10S)-6,7-difluoro-5,10-dihydrothieno[3,2-c] [2]benzothiepin-10-yl]-3,4,12,12a-tetrahydro-1H-[1,4] oxazino[3,4-c]pyrido[2,1-f][1,2,4]triazine-6,8-dione of general formula 1.2, (12aR)-12-[(10R)-6,7-difluoro-5,10-dihydrothieno[3,2-c] [2]benzothiepin-10-yl]-3,4,12,12a-tetrahydro-1H-[1,4] oxazino[3,4-c]pyrido[2,1-f][1,2,4]triazine-6,8-dione of general formula 1.3, its stereoisomer, their prodrug, pharmaceutically acceptable salt, solvate, hydrate, and a crystalline or polycrystalline form thereof.

1.1

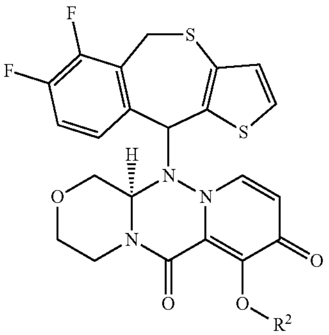

1.2

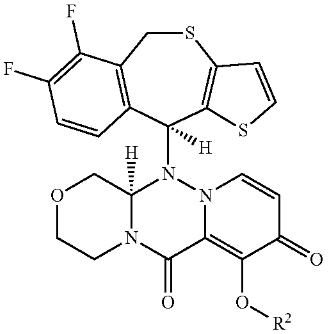

1.3

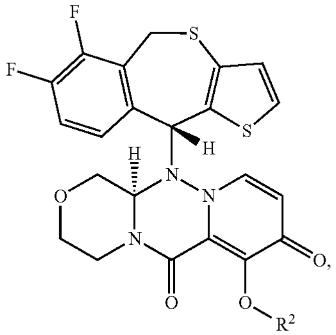

where $R^2$ has the above value.

More preferable compounds are:

(12aR)-7-benzyloxy-12-(6,7-difluoro-5,10-dihydrothieno[3,2-c][2]benzothiepin-10-yl)-3,4,12,12a-tetrahydro-1H-[1,4] oxazino[3,4-c]pyrido[2,1-f][1,2,4]triazine-6,8-dione (1.1.1), (12aR)-7-benzyloxy-12-[(10S)-6,7-difluoro-5,10-dihydrothieno[3,2-c][2]benzothiepin-10-yl]-3,4,12,12a-tetrahydro-1H-[1,4]oxazino[3,4-c]pyrido[2,1-J][1,2,4]triazine-6,8-dione (1.2.1), (12aR)-7-benzyloxy-12-[(10R)-6,7-difluoro-5,10-dihydrothieno[3,2-c][2]benzothiepin-10-yl]-3,4,12,12a-tetrahydro-1H-[1,4]oxazino[3,4-c]pyrido[2,1-f][1,2,4]triazine-6,8-dione (1.3.1), (12aR)-7-hydroxy-12-(6,7-difluoro-5,10-dihydrothieno[3,2-c][2]benzothiepin-10-yl)-3,4,12,12a-tetrahydro-1H-[1,4]oxazino[3,4-c]pyrido[2,1-f][1,2,4]triazine-6,8-dione (1.1.2), (12aR)-7-hydroxy-12-[(10S)-6,7-difluoro-5,10-dihydrothieno[3,2-c][2]benzothiepin-10-yl]-3,4,12,12a-tetrahydro-1H-[1,4]oxazino[3,4-c]pyrido[2,1-f][1,2,4]triazine-6,8-dione (1.2.2), (12aR)-7-hydroxy-12-[(10R)-6,7-difluoro-5,10-dihydrothieno[3,2-c][2]benzothiepin-10-yl]-3,4,12,12a-tetrahydro-1H-[1,4]oxazino[3,4-c]pyrido[2,1-f][1,2,4]triazine-6,8-dione (1.3.2), (12aR)-12-(6,7-difluoro-5,10-dihydrothieno[3,2-c][2]benzothiepin-10-yl)-6,8-dioxo-3,4,12,12a-tetrahydro-1H-[1,4]oxazino[3,4-c]pyrido[2,1-f][1,2,4]triazin-7-yl methyl carbonate (1.1.3), (12aR)-12-[(10S)-6,7-difluoro-5,10-dihydrothieno[3,2-c][2]benzothiepin-10-yl]-6,8-dioxo-3,4,12,12a-tetrahydro-1H-[1,4]oxazino[3,4-c]pyrido[2,1-f][1,2,4]triazin-7-yl methyl carbonate (1.2.3), (12aR)-12-[(10R)-6,7-difluoro-5,10-dihydrothieno[3,2-c][2]benzothiepin-10-yl]-6,8-dioxo-3,4,12,12a-tetrahydro-1H-[1,4]oxazino[3,4-c]pyrido[2,1-f][1,2,4]triazin-7-yl methyl carbonate (1.3.3), {[(12aR)-12-(6,7-difluoro-5,10-dihydrothieno[3,2-c][2]benzothiepin-10-yl)-6,8-dioxo-3,4,12,12a-tetrahydro-1H-[1,4]oxazino[3,4-c]pyrido[2,1-f][1,2,4]triazin-7-yl]oxy}methyl methyl carbonate (1.1.4), ({(12aR)-12-[(10S)-6,7-difluoro-5,10-dihydrothieno[3,2-c][2]benzothiepin-10-yl]-6,8-dioxo-3,4,12,12a-tetrahydro-1H-[1,4]oxazino[3,4-c]pyrido[2,1-f][1,2,4]triazin-7-yl}oxy)methyl methyl carbonate (1.2.4), ({(12aR)-12-[(10R)-6,7-difluoro-5,10-dihydrothieno[3,2-c][2]benzothiepin-10-yl]-6,8-dioxo-3,4,12,12a-tetrahydro-1H-[1,4]oxazino[3,4-c]pyrido[2,1-f][1,2,4]triazin-7-yl}oxy)methyl methyl carbonate (1.3.4), their stereoisomer, their prodrug, pharmaceutically acceptable salt, solvate, hydrate, and a crystalline or polycrystalline form thereof 1.1.1

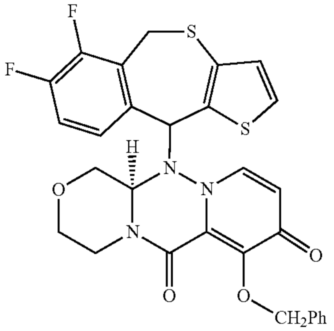

1.1.1

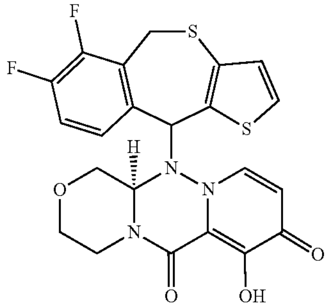

-continued
1.1.3
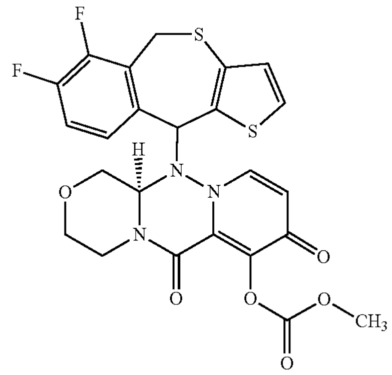
1.1.4
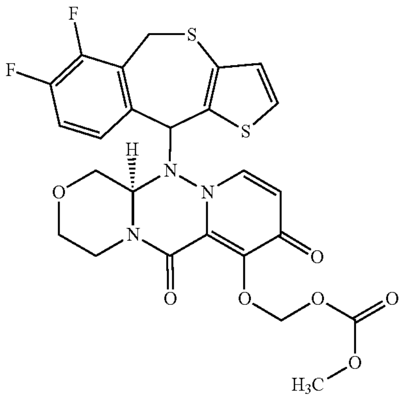
1.2.1
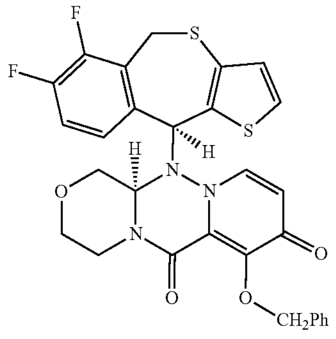
1.2.2
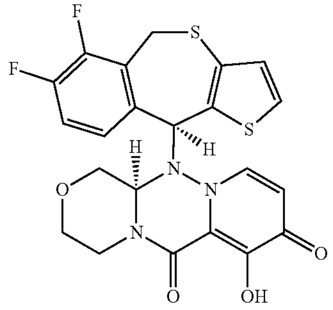
-continued
1.2.3
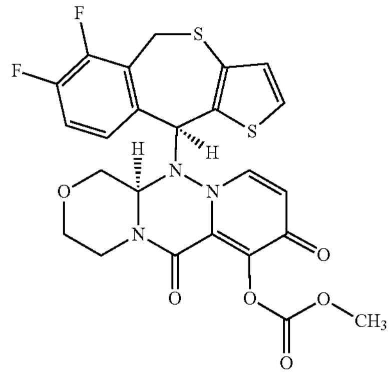
1.2.4
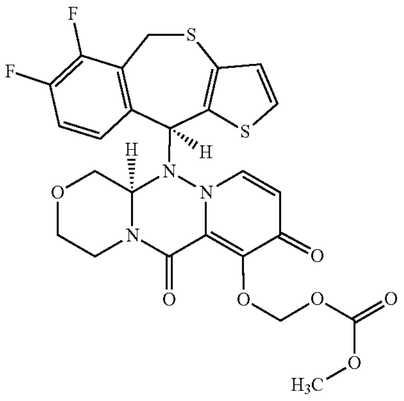
1.3.1
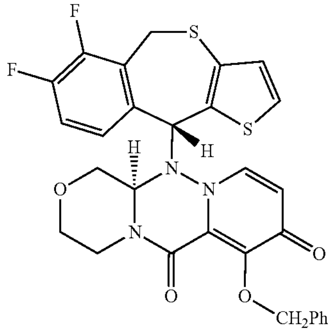
1.3.2
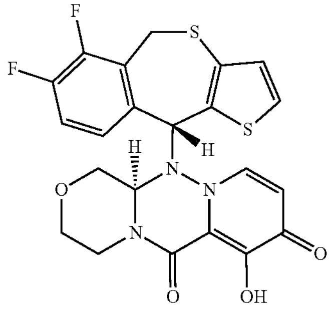

-continued 1.3.3

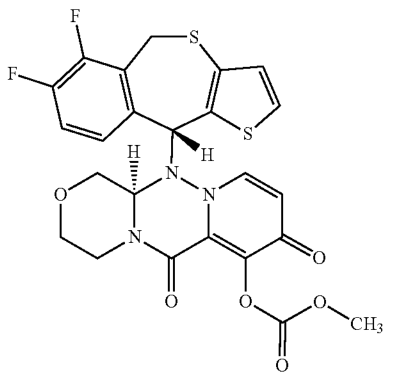

1.3.4

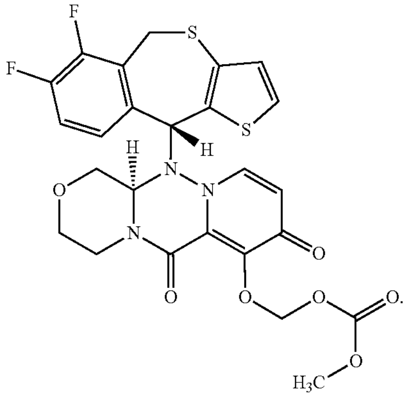

Preferable compounds are:

(12aR)-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4] triazine-6,8-dione of general formula 1.4, (12aR)-12-[(10S)-7,8-difluoro-4,9-dihydrothieno[2,3-c][2]benzothiepin-4-yl]-3,4,12,12a-tetrahydro-1H-[1,4]oxazino[3,4-c]pyrido[2,1-f][1,2,4] triazine-6,8-dione of general formula 1.5, (12aR)-12-[(10R)-7,8-difluoro-4,9-dihydrothieno[2,3-c][2]benzothiepin-4-yl]-3,4,12,12a-tetrahydro-1H-[1,4]oxazino[3,4-c]pyrido[2,1-f][1,2,4] triazine-6,8-dione of general formula 1.6, its stereoisomer, their prodrug, pharmaceutically acceptable salt, solvate, hydrate, and a crystalline or polycrystalline form thereof 1.4

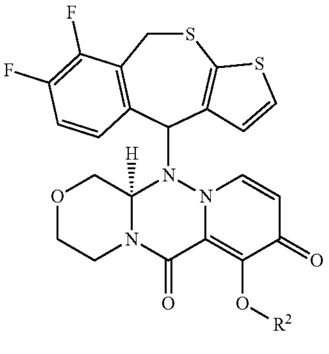

-continued 1.5

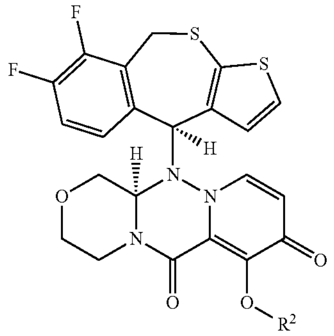

1.6

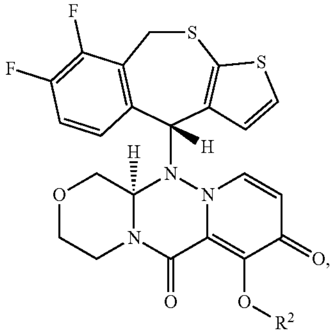

where $R^2$ has the above value.

More preferable compounds are:

(12aR)-7-benzyloxy-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4]triazine-6,8-dione 1.4.1, (12aR)-7-benzyloxy-12-[(10S)-7,8-difluoro-4,9-dihydrothieno[2,3-c][2]benzothiepin-4-yl]-3,4,12,12a-tetrahydro-1H-[1,4]oxazino[3,4-c]pyrido[2,1-f][1,2,4]triazine-6,8-dione 1.5.1, (12aR)-7-benzyloxy-12-[(10R)-7,8-difluoro-4,9-dihydrothieno[2,3-c][2]benzothiepin-4-yl]-3,4,12,12a-tetrahydro-1H-[1,4]oxazino[3,4-c]pyrido[2,1-f][1,2,4]triazine-6,8-dione 1.6.1, (12aR)-7-hydroxy-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4]triazine-6,8-dione 1.4.2, (12aR)-7-hydroxy-12-[(10S)-7,8-difluoro-4,9-dihydrothieno[2,3-c][2]benzothiepin-4-yl]-3,4,12,12a-tetrahydro-1H-[1,4]oxazino[3,4-c]pyrido[2,1-f][1,2,4]triazine-6,8-dione 1.5.2, (12aR)-7-hydroxy-12-[(10R)-7,8-difluoro-4,9-dihydrothieno[2,3-c][2]benzothiepin-4-yl]-3,4,12,12a-tetrahydro-1H-[1,4]oxazino[3,4-c]pyrido[2,1-f][1,2,4]triazine-6,8-dione 1.6.2, (12aR)-12-(7,8-difluoro-4,9-dihydrothieno[2,3-c][2]benzothiepin-4-yl)-6,8-dioxo-3,4,12,12a-tetrahydro-1H-[1,4]oxazino[3,4-c]pyrido[2,1-f][1,2,4]triazin-7-yl methyl carbonate 1.4.3, (12aR)-12-[(10S)-7,8-difluoro-4,9-dihydrothieno[2,3-c][2]benzothiepin-4-yl]-6,8-dioxo-3,4,12,12a-tetrahydro-1H-[1,4]oxazino[3,4-c]pyrido[2,1-f][1,2,4]triazin-7-yl methyl carbonate 1.5.3, (12aR)-12-[(10R)-7,8-difluoro-4,9-dihydrothieno[2,3-c][2]benzothiepin-4-yl]-6,8-dioxo-3,4,12,12a-tetrahydro-1H-[1,4]oxazino[3,4-c]pyrido[2,1-f][1,2,4]triazin-7-yl methyl carbonate 1.6.3, {[(12aR)-12-(7,8-difluoro-4,9-dihydrothieno[2,3-c][2]benzothiepin-4-yl)-6,8-dioxo-3,4,12,12a-tetrahydro-1H-[1,4]oxazino[3,4-c]pyrido[2,1-f][1,2,4]triazin-7-yl]oxy}methyl methyl carbonate 1.4.4, {[(12aR)-12-[(10S)-7,8-difluoro-4,9-dihydrothieno[2,3-c][2]benzothiepin-4-yl]-6,8-dioxo-3,4,12,12a-tetrahydro-1H-[1,4]oxazino[3,4-c]pyrido[2,1-f][1,2,4]triazin-7-yl]oxy}methyl methyl carbonate 1.5.4, {[(12aR)-12-[(10R)-7,8-difluoro-4,9-dihydrothieno[2,3-c][2]benzothiepin-4-yl]-6,8-dioxo-3,4,12,12a-tetrahydro-1H-[1,4]oxazino[3,4-c]pyrido[2,1-f][1,2,4]triazin-7-yl]oxy}methyl methyl carbonate 1.6.4, its stereoisomer, their prodrug, pharmaceutically acceptable salt, solvate, hydrate, and a crystalline or polycrystalline form thereof 1.4.1

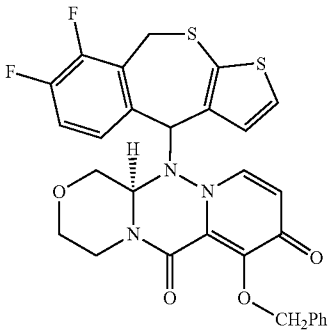

1.4.2

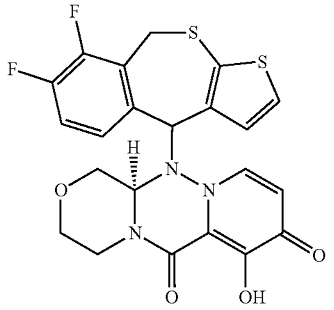

1.4.3

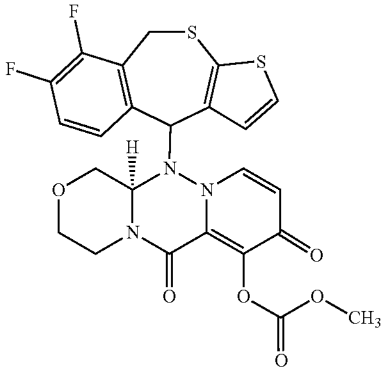

-continued 1.4.4

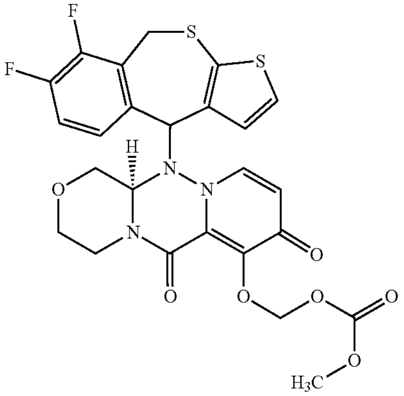

1.5.1

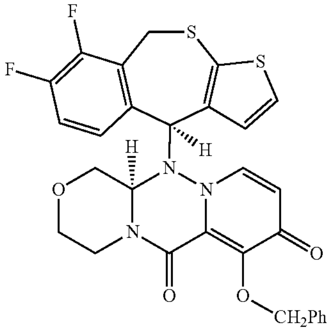

1.5.2

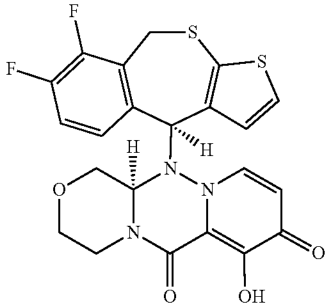

1.5.3

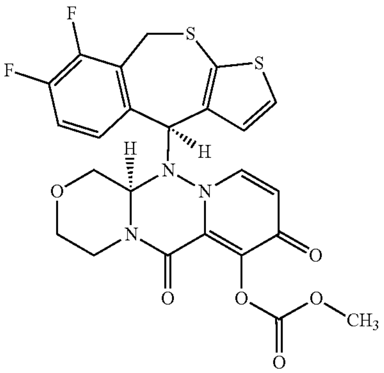

-continued 1.5.4

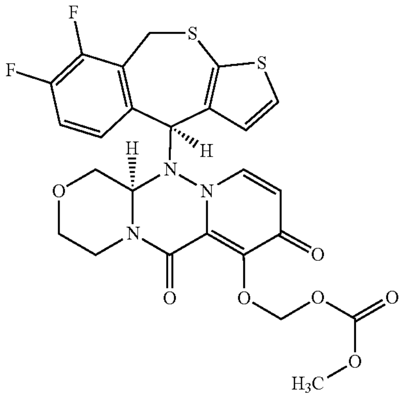

1.6.1

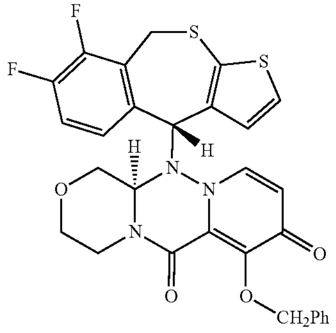

1.6.2

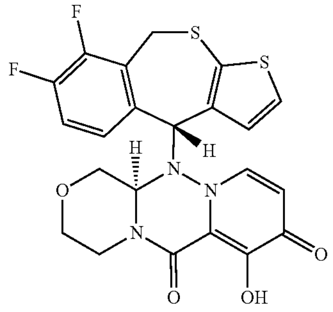

1.6.3

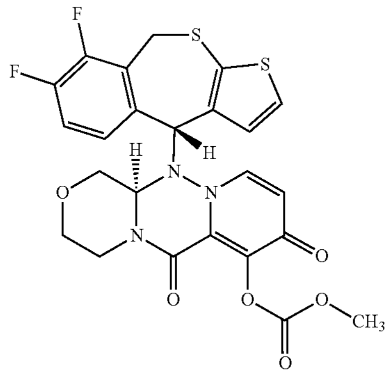

-continued 1.6.4

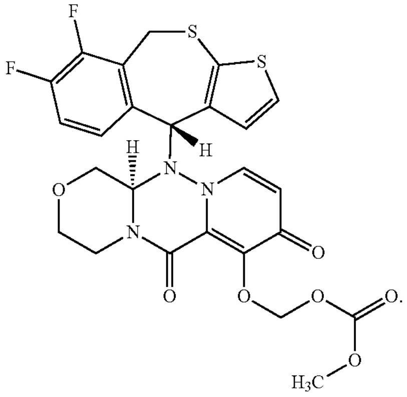

Preferable compounds are:

(12aR)-12-[(3,4-difluorophenyl)(phenyl)methyl]-3,4,12,12a-tetrahydro-1H-[1,4]oxazino[3,4-c]pyrido[2,1-f][1,2,4]triazine-6,8-dione of general formula 1.7, (12aR)-12-[(R)-(3,4-difluorophenyl)(phenyl)methyl]-3,4,12,12a-tetrahydro-1H-[1,4]oxazino[3,4-c]pyrido[2,1-f][1,2,4]triazine-6,8-dione of general formula 1.8, (12aR)-12-[(S)-(3,4-difluorophenyl)(phenyl)methyl]-3,4,12,12a-tetrahydro-1H-[1,4]oxazino[3,4-c]pyrido[2,1-f][1,2,4]triazine-6,8-dione of general formula 1.9, its stereoisomer, their prodrug, pharmaceutically acceptable salt, solvate, hydrate, and a crystalline or polycrystalline form thereof 1.7

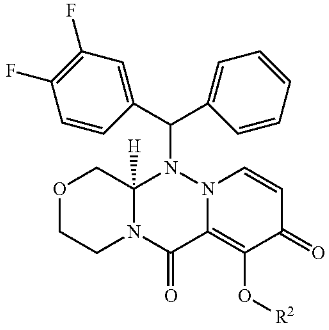

1.8

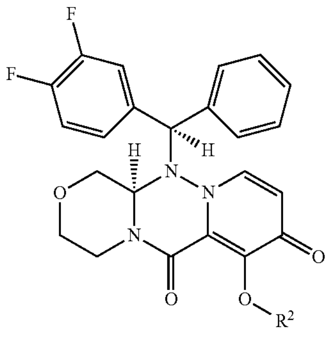

-continued 1.9

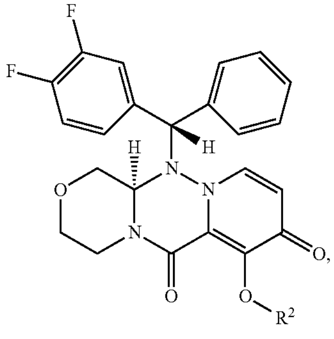

where $R^2$ has the above value.

More preferable compounds are:

(12aR)-7-benzyloxy-12-[(3,4-difluorophenyl)(phenyl) methyl]-3,4,12,12a-tetrahydro-1H-[1,4]oxazino[3,4-c] pyrido[2,1-f][1,2,4]triazine-6,8-dione (1.7.1), (12aR)-7-benzyloxy-12-[(R)-(3,4-difluorophenyl)(phenyl) methyl]-3,4,12,12a-tetrahydro-1H-[1,4]oxazino[3,4-c] pyrido[2,1-f][1,2,4]triazine-6,8-dione (1.8.1), (12aR)-7-benzyloxy-12-[(S)-(3,4-difluorophenyl)(phenyl) methyl]-3,4,12,12a-tetrahydro-1H-[1,4]oxazino[3,4-c] pyrido[2,1-f][1,2,4]triazine-6,8-dione (1.9.1), (12aR)-7-hydroxy-12-[(3,4-difluorophenyl)(phenyl) methyl]-3,4,12,12a-tetrahydro-1H-[1,4]oxazino[3,4-c] pyrido[2,1-f][1,2,4]triazine-6,8-dione (1.7.2), (12aR)-7-hydroxy-12-[(R)-(3,4-difluorophenyl)(phenyl) methyl]-3,4,12,12a-tetrahydro-1H-[1,4]oxazino[3,4-c] pyrido[2,1-f][1,2,4]triazine-6,8-dione (1.8.2), (12aR)-7-hydroxy-12-[(S)-(3,4-difluorophenyl)(phenyl) methyl]-3,4,12,12a-tetrahydro-1H-[1,4]oxazino[3,4-c] pyrido[2,1-f][1,2,4]triazine-6,8-dione (1.9.2), (12aR)-12-[(3,4-difluorophenyl)(phenyl)methyl]-6,8-dioxo-3,4,12,12a-tetrahydro-1H-[1,4]oxazino[3,4-c]pyrido[2,1-f][1,2,4]triazin-7-yl methyl carbonate (1.7.3), (12aR)-12-[(R)-(3,4-difluorophenyl)(phenyl)methyl]-6,8-dioxo-3,4,12,12a-tetrahydro-1H-[1,4]oxazino[3,4-c] pyrido[2,1-f][1,2,4]triazin-7-yl methyl carbonate (1.8.3), (12aR)-12-[(S)-(3,4-difluorophenyl)(phenyl)methyl]-3,4,12,12a-tetrahydro-1H-[1,4]oxazino[3,4-c]pyrido[2,1-f][1,2,4]triazin-7-yl methyl carbonate (1.9.3), ({(12aR)-12-[(3,4-difluorophenyl)(phenyl)methyl]-6,8-dioxo-3,4,12,12a-tetrahydro-1H-[1,4]oxazino[3,4-c]pyrido[2,1-f][1,2,4]triazin-7-yl}oxy)methyl methyl carbonate (1.7.4), ({(12aR)-12-[(R)-(3,4-difluorophenyl)(phenyl)methyl]-6,8-dioxo-3,4,12,12a-tetrahydro-1H-[1,4]oxazino[3,4-c] pyrido[2,1-f][1,2,4]triazin-7-yl}oxy)methyl methyl carbonate (1.8.4), ({(12aR)-12-[(S)-(3,4-difluorophenyl) (phenyl)methyl]-3,4,12,12a-tetrahydro-1H-[1,4]oxazino[3,4-c]pyrido[2,1-f][1,2,4]triazin-7-yl}oxy)methyl methyl carbonate (1.9.4), its stereoisomer, their prodrug, pharmaceutically acceptable salt, solvate, hydrate, and a crystalline or polycrystalline form thereof 1.7.1

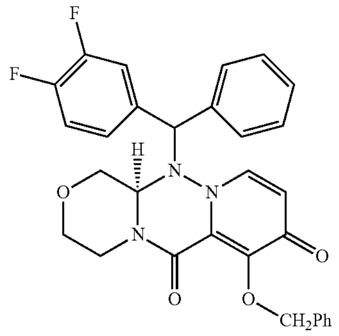

1.7.2

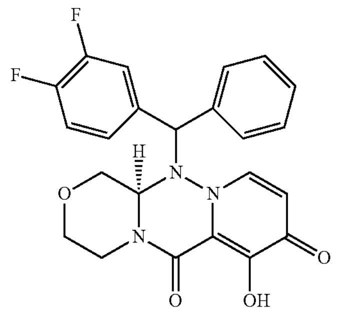

1.7.3

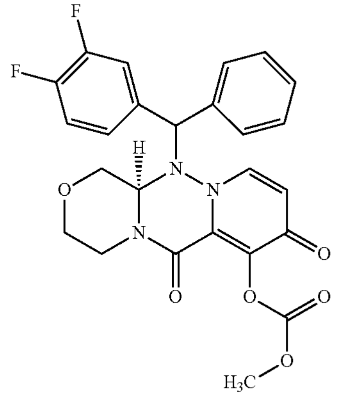

1.7.4

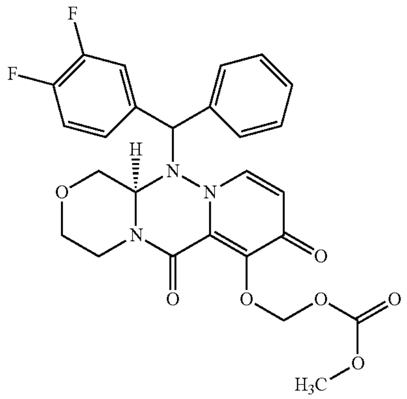

-continued
1.8.1
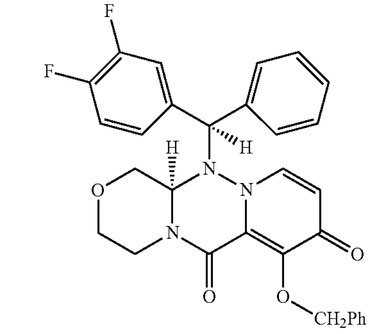
1.8.2
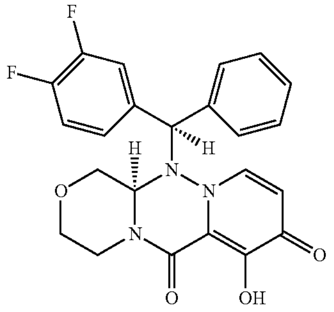
1.8.3
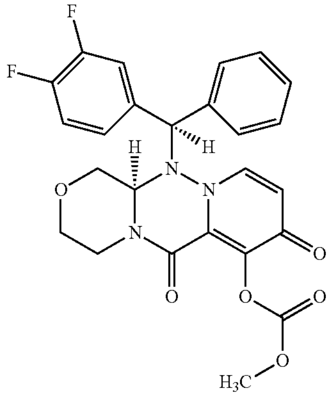
1.8.4
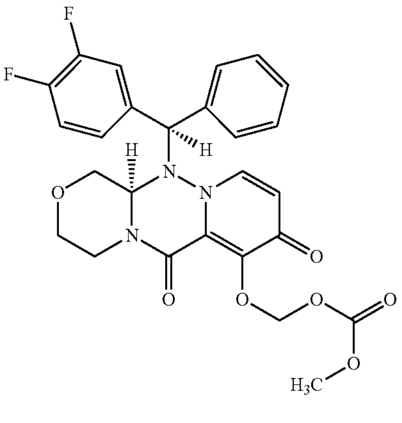
-continued
1.9.1
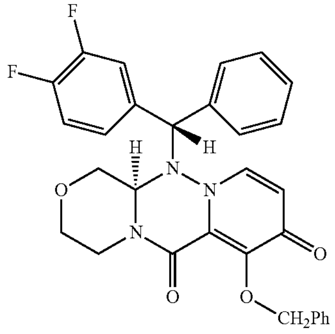
1.9.2
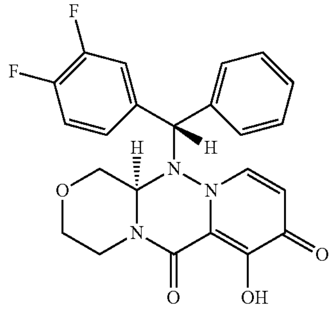
1.9.3
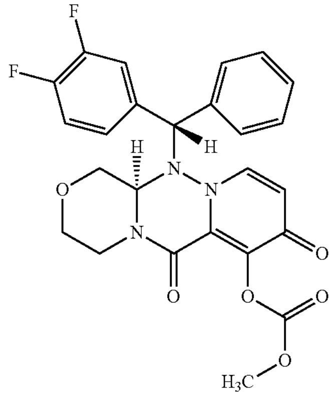
1.9.4
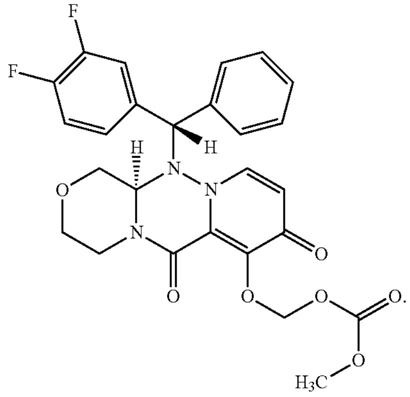
Preferable compounds are:
(12aR)-12-[(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione of general formula 1.10, (12aR)-12-[(R)-(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione of general formula 1.11, (12aR)-12-[(S)-(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione of general formula 1.12, its stereoisomer, their prodrug, pharmaceutically acceptable salt, solvate, hydrate, and a crystalline or polycrystalline form thereof 1.10

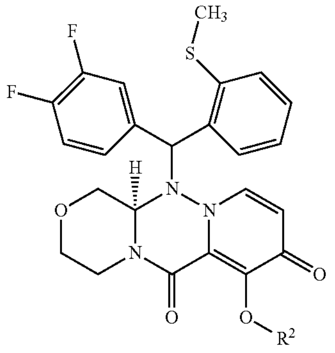

1.11

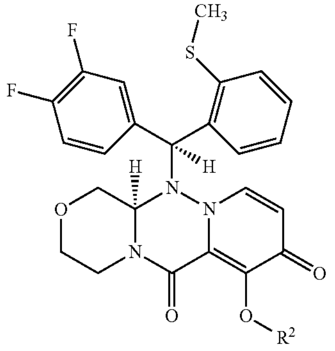

1.12

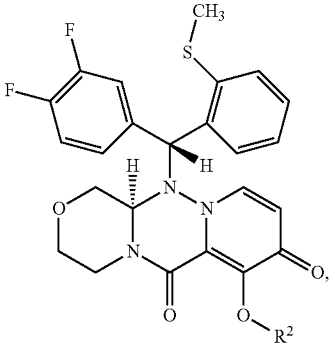

where $R^2$ has the above value.

More preferable compounds are:

(12aR)-7-benzyloxy-12-[(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione (1.10.1), (12aR)-7-benzyloxy-12-[(R)-(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione (1.11.1), (12aR)-7-benzyloxy-12-[(S)-(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione (1.12.1), (12aR)-7-hydroxy-12-[(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione (1.10.2), (12aR)-7-hydroxy-12-[(R)-(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione (1.11.2), (12aR)-7-hydroxy-12-[(S)-(3,4-difluorophenyl)(2-methylsulfanylphenyl)methyl]-3,4,12,12a-tetrahydro-1H-[1,4]oxazino[3,4-c]pyrido[2,1-f][1,2,4]triazine-6,8-dione (1.12.2), (12aR)-12-[(3,4-difluorophenyl)(2-methylsulfanylphenyl)methyl]-6,8-dioxo-3,4,12,12a-tetrahydro-1H-[1,4]oxazino[3,4-c]pyrido[2,1-f][1,2,4]triazin-7-yl methyl carbonate (1.10.3), (12aR)-12-[(R)-(3,4-difluorophenyl)(2-methylsulfanylphenyl)methyl]-6,8-dioxo-3,4,12,12a-tetrahydro-1H-[1,4]oxazino[3,4-c]pyrido[2,1-f][1,2,4]triazin-7-yl methyl carbonate (1.11.3), (12aR)-12-[(S)-(3,4-difluorophenyl)(2-methylsulfanylphenyl)methyl]-3,4,12,12a-tetrahydro-1H-[1,4]oxazino[3,4-c]pyrido[2,1-f][1,2,4]triazin-7-yl methyl carbonate (1.12.3), ({(12aR)-12-[(3,4-difluorophenyl)(2-methylsulfanylphenyl)methyl]-6,8-dioxo-3,4,12,12a-tetrahydro-1H-[1,4]oxazino[3,4-c]pyrido[2,1-f][1,2,4]triazin-7-yl}oxy)methyl methyl carbonate (1.10.4), ({(12aR)-12-[(R)-(3,4-difluorophenyl)(2-methylsulfanylphenyl)methyl]-6,8-dioxo-3,4,12,12a-tetrahydro-1H-[1,4]oxazino[3,4-c]pyrido[2,1-f][1,2,4]triazin-7-yl}oxy)methyl methyl carbonate (1.11.4), ({(12aR)-12-[(S)-(3,4-difluorophenyl)(2-methylsulfanylphenyl)methyl]-3,4,12,12a-tetrahydro-1H-[1,4]oxazino[3,4-c]pyrido[2,1-f][1,2,4]triazin-7-yl}oxy)methyl methyl carbonate (1.12.4), their stereoisomer, their prodrug, pharmaceutically acceptable salt, solvate, hydrate, and a crystalline or polycrystalline form thereof 1.10.1

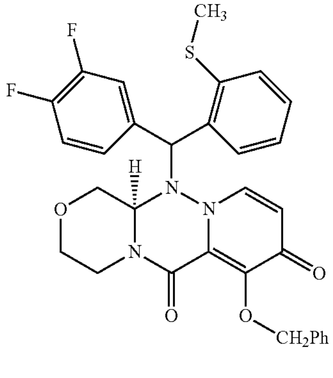

-continued
1.10.2
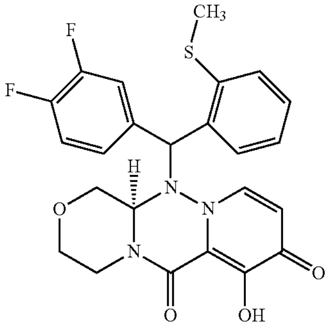
1.10.3
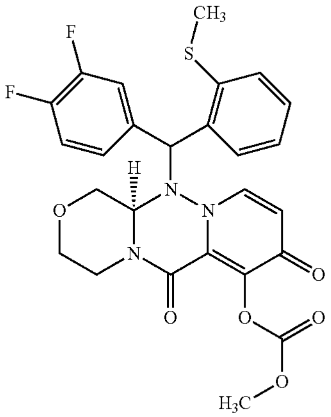
1.10.4
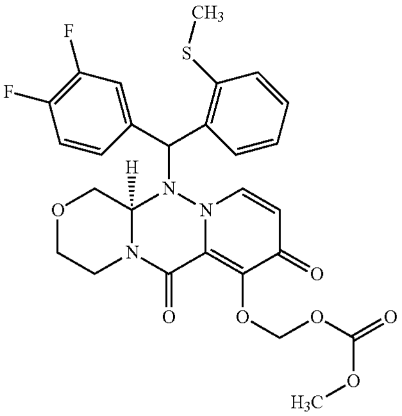
1.11.1
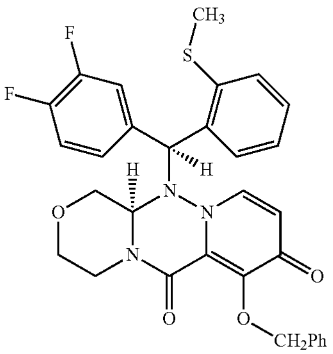
-continued
1.11.2
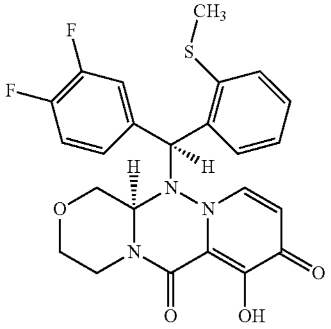
1.11.3
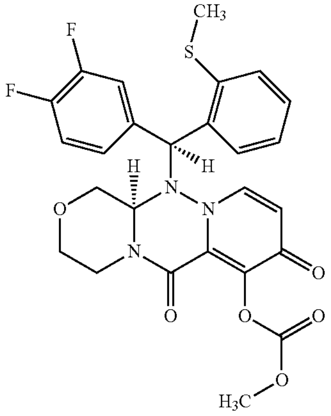
1.11.4
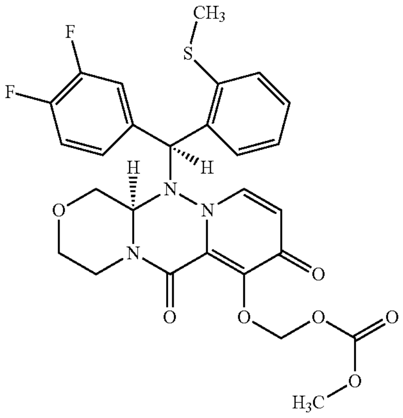
1.12.1
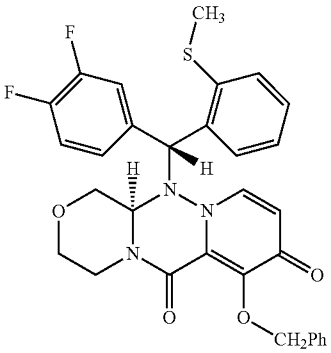

-continued 1.12.2

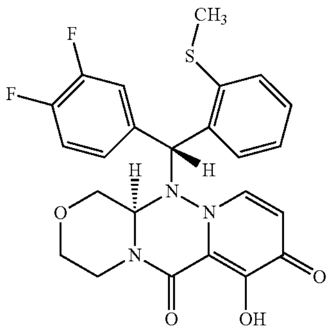

1.12.3

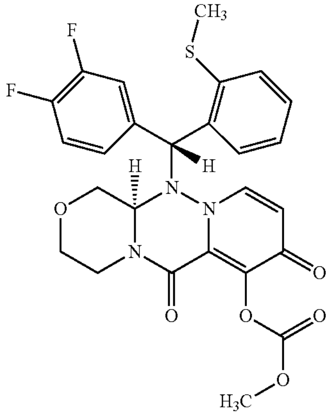

1.12.4

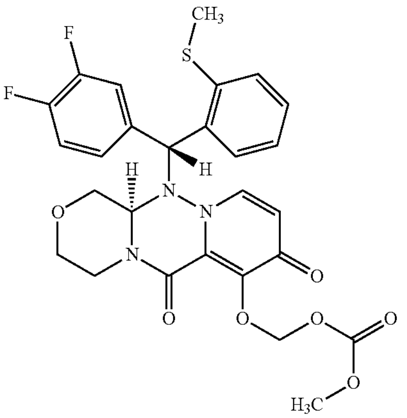

Preferable compounds are:

(12aR)-12-diphenylmethyl-3,4,12,12a-tetrahydro-1H-[1,4]oxazino[3,4-c]pyrido[2,1-f][1,2,4]triazine-6,8-dione of general formula 1.13, its stereoisomer, their prodrug, pharmaceutically acceptable salt, solvate, hydrate, and a crystalline or polycrystalline form thereof 1.13

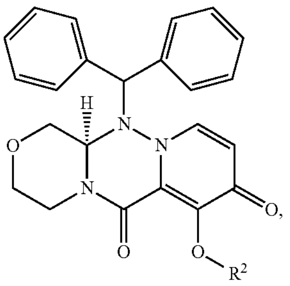

where $R^2$ has the above value.

More preferable compounds are:

(12aR)-7-benzyloxy-12-diphenylmethyl-3,4,12,12a-tetrahydro-1H-[1,4]oxazino[3,4-c]pyrido[2,1-f][1,2,4]triazine-6,8-dione (1.13.1), (12aR)-7-hydroxy-12-diphenylmethyl-3,4,12,12a-tetrahydro-1H-[1,4]oxazino[3,4-c]pyrido[2,1-f][1,2,4]triazine-6,8-dione (1.13.2), (12aR)-12-diphenylmethyl-6,8-dioxo-3,4,12,12a-tetrahydro-1H-[1,4]oxazino[3,4-c]pyrido[2,1-f][1,2,4]triazin-7-yl methyl carbonate (1.13.3), ({(12aR)-12-diphenylmethyl-3,4,12,12a-tetrahydro-1H-[1,4]oxazino[3,4-c]pyrido[2,1-f][1,2,4]triazin-7-yl}oxy) methyl methyl carbonate (1.13.4), its stereoisomer, their prodrug, pharmaceutically acceptable salt, solvate, hydrate, and a crystalline or polycrystalline form thereof 1.13.1

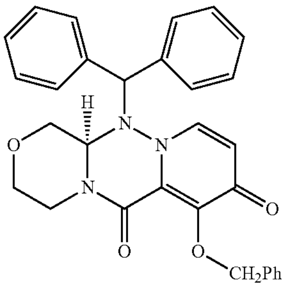

1.13.2

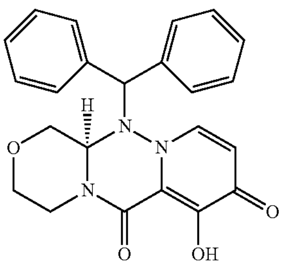

-continued 1.13.3

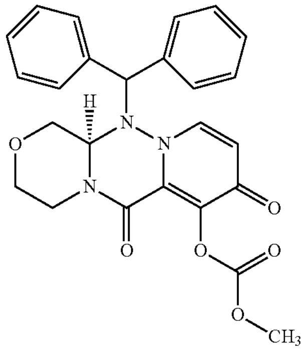

1.13.4

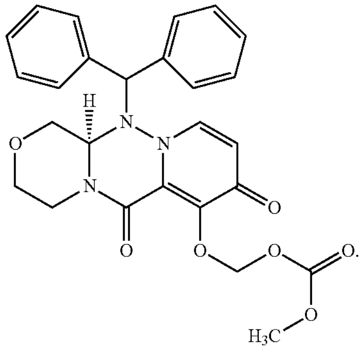

Preferable compounds are:

(12aR)-12-[bis(4-fluorophenyl)methyl]-3,4,12,12a-tetrahydro-1H-[1,4]oxazino[3,4-c]pyrido[2,1-f][1,2,4]triazine-6,8-dione of general formula 1.14, its stereoisomer, their prodrug, pharmaceutically acceptable salt, solvate, hydrate, and a crystalline or polycrystalline form thereof 1.14

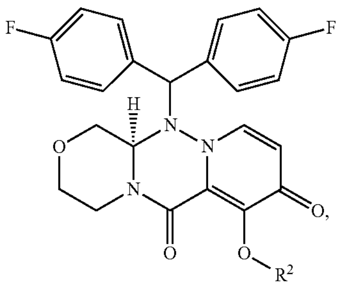

where $R^2$ has the above value.

More preferable compounds are:

(12aR)-7-benzyloxy-12-[bis(4-fluorophenyl) methyl]-3,4,12,12a-tetrahydro-1H-[1,4]oxazino[3,4-c]pyrido[2,1-f][1,2,4]triazine-6,8-dione (1.14.1), (12aR)-7-hydroxy-12-[bis(4-fluorophenyl) methyl]-3,4,12,12a-tetrahydro-1H-[1,4]oxazino[3,4-c]pyrido[2,1-f][1,2,4]triazine-6,8-dione (1.14.2), (12aR)-12-[bis(4-fluorophenyl) methyl]-6,8-dioxo-3,4,12,12a-tetrahydro-1H-[1,4]oxazino[3,4-c]pyrido[2,1-f][1,2,4]triazin-7-yl methyl carbonate (1.14.3), ({(12aR)-12-[bis(4-fluorophenyl) methyl]-3,4,12,12a-tetrahydro-1H-[1,4]oxazino[3,4-c]pyrido[2,1-f][1,2,4]triazin-7-yl}oxy)methyl methyl carbonate (1.14.4), its stereoisomer, their prodrug, pharmaceutically acceptable salt, solvate, hydrate, and a crystalline or polycrystalline form thereof 1.14.1

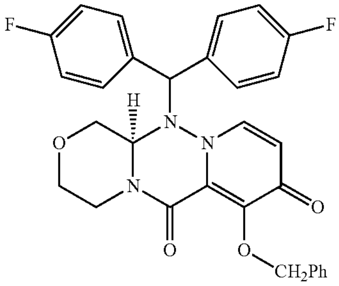

1.14.2

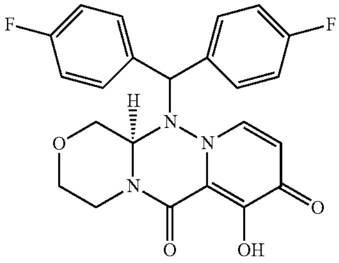

1.14.3

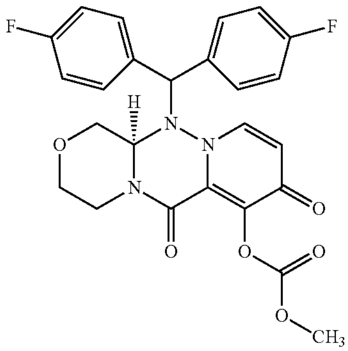

1.14.4

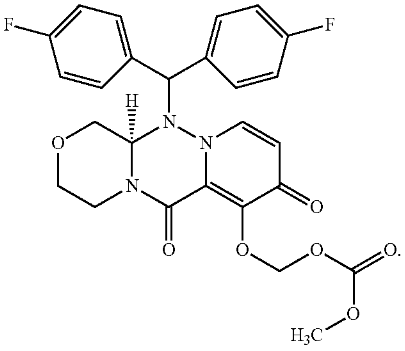

A further subject of this invention is a method for the production of compounds of general formula 1, including preparation of 7-benzyloxy derivatives 1.1.1-1.14.1 by interaction of (12aR)-7-(benzyloxy)-3,4,12,12a-tetrahydro-1H-[1,4]oxazino[3,4-c]-pyrido[2,1-f][1,2,4]triazine-6,8-dione (2) with 6,7-difluoro-5,10-dihydrothieno[3,2-c][2]benzothiepin-10-ol (3) or with 7,8-difluoro-7,8-dihydrothieno[2,3-c][2]benzothiepin-4-ol (4), or with (3,4-difluorophenyl)(phenyl)methanol (5), (3,4-difluorophenyl)(2-methylsulfanylphenyl)methanol (6), diphenylmethanol (7) or with bis(4-fluorophenyl)methanol (8), respectively

2

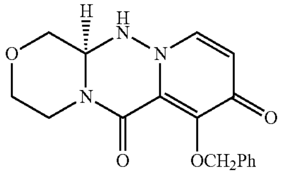

3

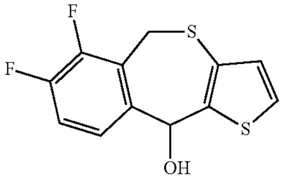

4

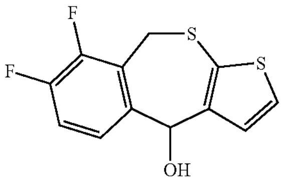

5

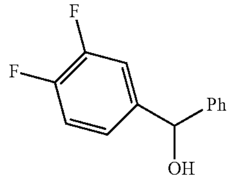

6

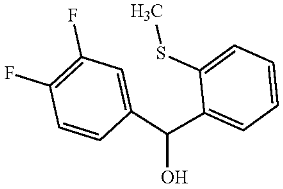

7

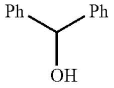

8

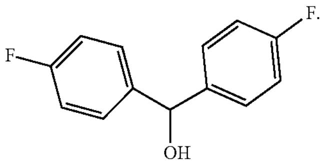

Figure 2:
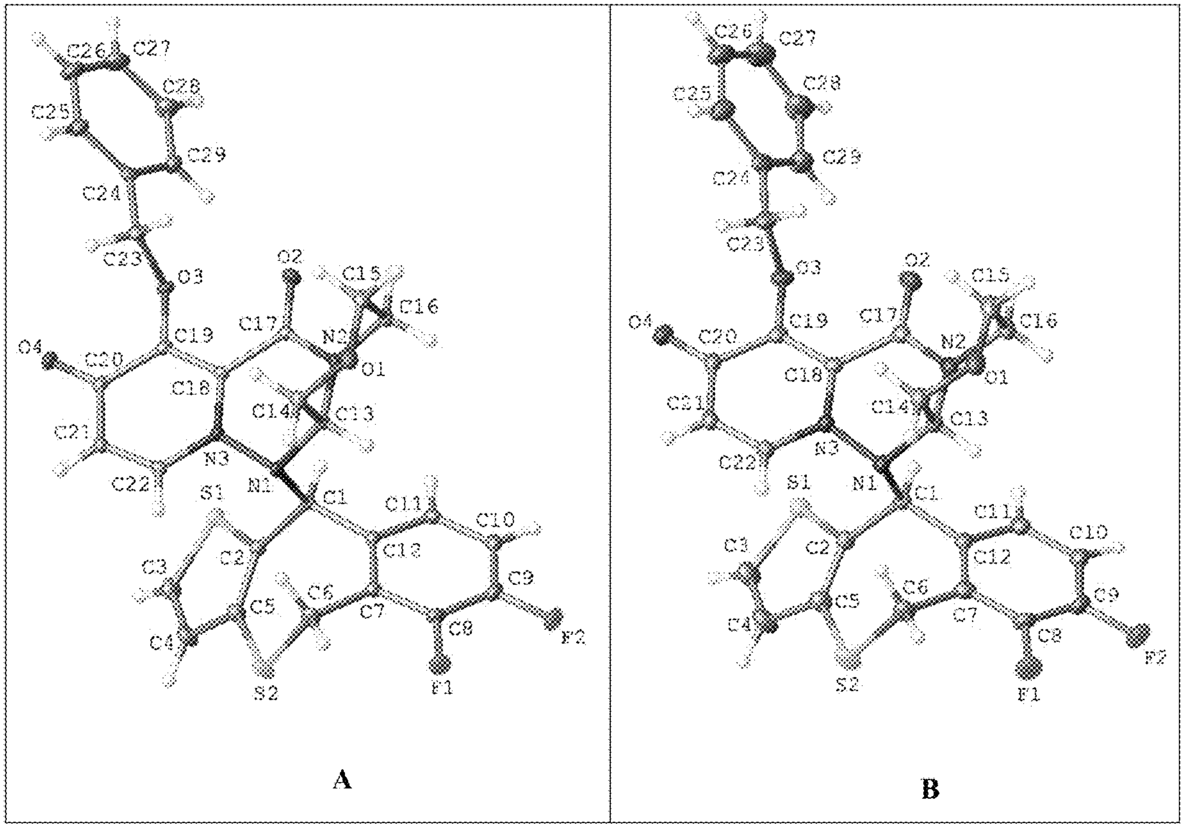

The resulting 7-benzyloxy derivatives 1.1.1, 1.4.1, 1.7.1, and 1.10.1 are separated into respective diastereoisomers 1.2.1, 1.3.1, 1.5.1, 1.6.1, 1.8.1, 1.9.1, 1.11.1, and 1.12.1 whose structure was confirmed by X-Ray Diffraction (XRD) data. Thus, diastereomer (12aR)-7-(benzyloxy)-12-[(10S)-5,10-dihydrothieno[3,2-c][2]benzothiepin-10-yl]-3,4,12,12a-tetrahydro-1H-[1,4]oxazino[3,4-c]pyrido[2,1-f][1,2,4]triazine-6,8-dione (1.2.1) was recrystallized from ethanol and isopropanol to give rhombic crystals that, according to XRD data, are corresponding solvates with ethanol 1.2.1·$C_2H_5OH$ and isopropanol 1.2.1·i-$C_3H_7OH$ in the ratios of 4:3 and 8:3 (FIGS. 1 and 2).

Figure 3:
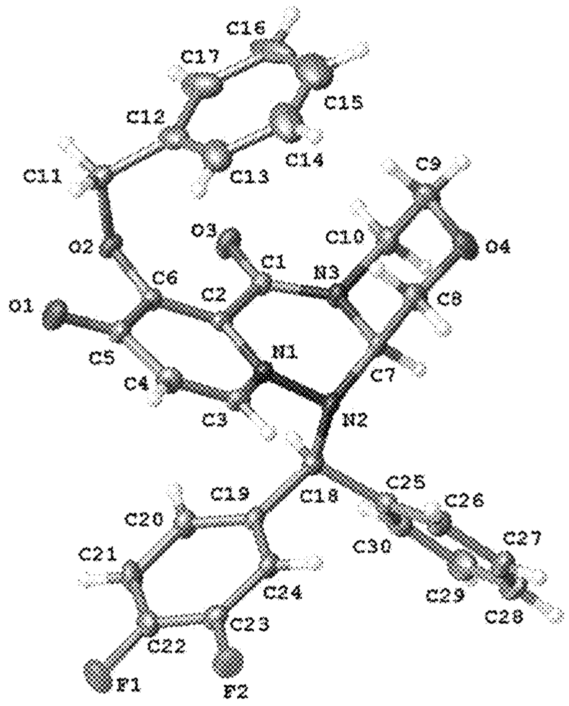
Figure 3:
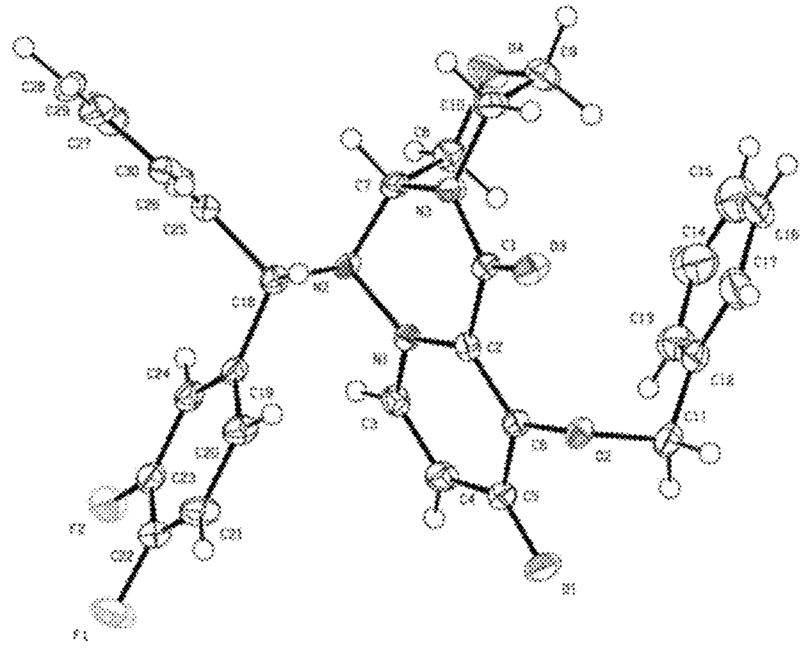

Diastereomer (12aR)-7-benzyloxy-12-[(S)-(3,4-difluorophenyl)(phenyl)methyl]-3,4,12,12a-tetrahydro-1H-[1,4]oxazino[3,4-c]pyrido[2,1-f][1,2,4]triazine-6,8-dione (1.9.1) was recrystallized from a dichloromethane-hexane mixture to give crystals that according to x ray diffraction analysis are referred to the triclinic crystal system (FIG. 3).

7-Benzyloxy derivatives 1.1.1-1.14.1 are debenzylated by heating in dimethyl sulfoxide in the presence of lithium chloride in corresponding 7-hydroxy derivatives 1.1.2-1.14.2, and the latter are converted into prodrugs 1.1.3-1.14.3 and 1.1.4-1.14.4. The parent 6,7-difluoro-5.10-dihydrothieno[3,2-c][2]benzothiepin-10-ol (3) is a novel compound, therefore said compound and the method of production thereof are also the subject of the present invention. According to the invention, the method for producing 6,7-difluoro-5,10-dihydrothieno[3,2-c][2]benzothiepin-10-ol (3) involves cyclization of 3,4-difluoro-2-[(3-thienylthio)methyl]-benzoic acid (3.6) in the presence of $PCl_5$ and the reduction of the resulting 6,7-difluoro-5,10-dihydrothieno[3,2-c][2]benzothiepin-10(5H)-one (3.7) by sodium borohydride (Scheme 1).

Scheme 1. Synthesis of 6,7-difluoro-5,10-dihydrothieno[3,2-c][2]benzothiepin-10-ol (3).

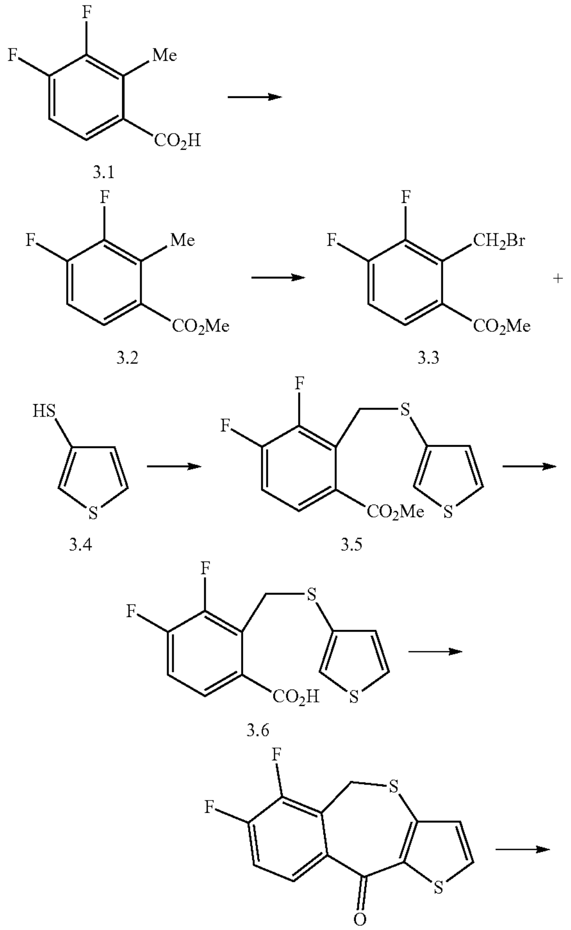

3.1 3.2 3.3 3.4 3.5 3.6 3.7 3

The parent 7,8-difluoro-7,8-dihydrothieno[2,3-c][2]benzothiepin-10-ol (4) is a novel compound, therefore said compound and the method of production thereof are also the subject of the present invention.

According to the invention, the method for producing 7,8-difluoro-7,8-dihydrothieno[2,3-c][2]benzothiepin-10-ol (4) involves cyclization of 3,4-difluoro-2-[(3-thienylthio)

methyl]-benzoic acid (4.3) in the presence of $PCl_5$ and reduction of the resulting 6,7-difluoro-5,10-dihydrothieno [3,2-c][2]benzothiepin-10(5H)-one (4.4) by sodium borohydride (Scheme 2).

Scheme 2. Synthesis of 7,8-difluoro-7,8-dihydroieno [2,3-c][2]benzothiepin-10-ol (4)

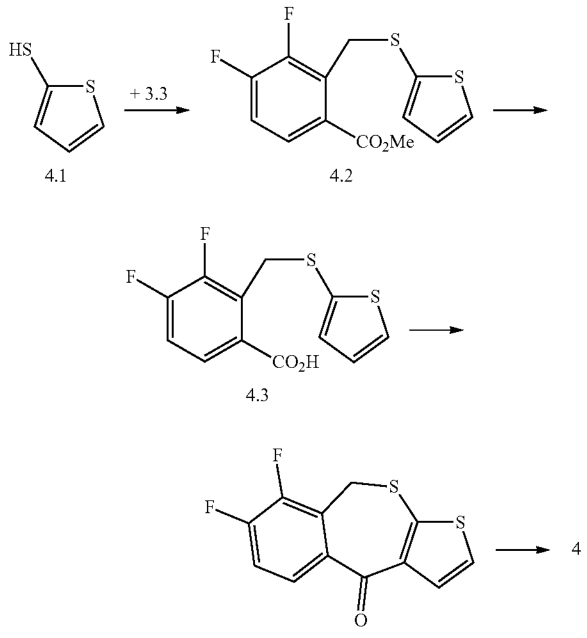

4.1

4.2

4.3

4.4

4

The parent (3,4-difluorophenyl)(phenyl)methanol (5) is a novel compound, therefore said compound and the method of production thereof are also the subject of the present invention.

According to the invention, the method for producing (3,4-difluorophenyl)(phenyl)methanol (5) involves reduction of 3,4-difluorobenzophenone (5.1) by sodium borohydride (Scheme 3).

Scheme 3. Synthesis of (3,4-difluorophenyl)(phenyl)methanol (5).

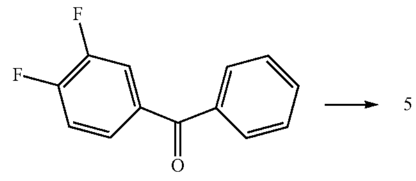

5.1

5

The parent (3,4-difluorophenyl)(2-methylsulfanylphenyl) methanol (6) is a novel compound, therefore said compound and the method of production thereof are also the subject of the present invention. According to the invention, the method for producing (3,4-difluorophenyl)(2-methylsulfanylphenyl)methanol (6) involves reduction of (3,4-difluorophenyl)[2-methylsulfanyl)phenyl]methanone (6.6) by sodium borohydride (Scheme 4).

Scheme 4. Synthesis of (3,4-difluorophenyl)(2-methylsulfanylphenyl)methanol (6).

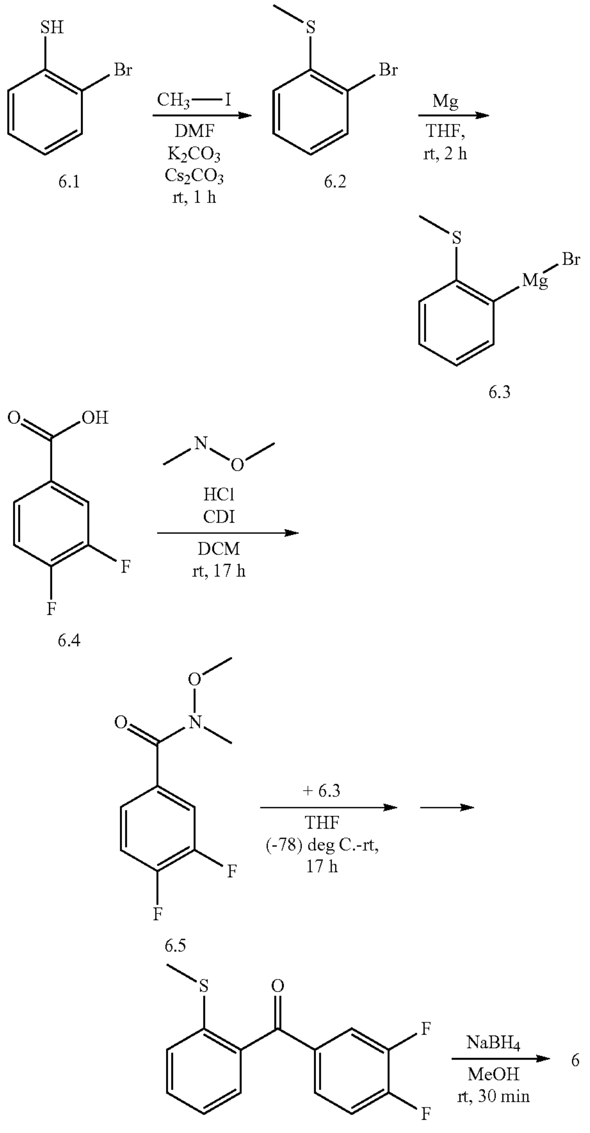

6.1

6.2

6.3

6.4

6.5

6.6

6

The novel 7-hydroxy-3,4,12,12a-tetrahydro-1H-[1,4] oxazino[3,4-c]pyrido[2,1-f][1,2,4]triazine-6,8-diones containing at position 12 diarylmethyl substituents, unlike Baloxavir (BXA), are orally available inhibitors of the influenza virus with a fairly high bioavailability. At the same time, Cmax and AUClast of said inhibitors are 1-2 orders of magnitude better than those of BXA.

TABLE 1

Pharmacokinetic parameters in mouse plasma following the administration of drugs at a dose of 15 mg/kg

| Drug | 1.8.2 | 1.9.2 | 1.13.2 | 1.14.4 | BXA |
|---|---|---|---|---|---|
| Control | 1.8.2 | 1.9.2 | 1.13.2 | 1.14.4 | BXA |
| Kel, 1/h | 0.25 | 0.27 | 0.24 | 0.27 | 0.19 |
| T1/2, h | 2.75 | 2.56 | 2.91 | 2.55 | 3.74 |
| Tmax, h | 1 | 1 | 0.5 | 2 | 4 |
| Cmax, ng/ml | 2090 | 2375 | 684 | 308 | 11.9 |

TABLE 1-continued

| Pharmacokinetic parameters in mouse plasma following the administration of drugs at a dose of 15 mg/kg | | | | | |
|---|---|---|---|---|---|
| AUClast, h · ng/ml | 9448 | 10958 | 2,657 | 1,822 | 80 |
| AUCINF, h · ng/ml | 9469 | 10977 | 2,661 | 2,069 | 95 |
| MRTlast, h | 3.48 | 3.34 | 2.64 | 3.23 | 4.79 |
| $F_{AUClast}$, % | NDA* | NDA* | 42 | 23 | NDA* |

Kel - elimination constant;
T1/2 - elimination half-life;
AUClast - Area under the concentration-time curve from time zero to the last quantifiable concentration;
AUCinf - area under the pharmacokinetic curve (concentration-time curve) from time zero to infinity; and
MRTlast is the mean residence time in the body from time zero to the last quantifiable concentration.

The pharmacokinetic parameters, in particular, Cmax and AUClast, in mouse plasma following the administration of novel proinhibitors (Table 2) are 10-40 times higher than those of Baloxavir Marboxil (BXM).

TABLE 2

Pharmacokinetic parameters in mouse plasma following the administration of drugs at a dose of 15 mg/kg

| Drug | 1.3.4 | 1.8.4 | 1.9.4 | 1.13.4 | 1.14.4 | 5101 |
|---|---|---|---|---|---|---|
| Control | 1.3.2 | 1.8.2 | 1.9.2 | 1.13.2 | 1.14.4 | 5107 |
| Kel, 1/h | 0.25 | 0.25 | 0.26 | 0.30 | 0.74 | 0.17 |
| T½, h | 2.74 | 2.75 | 2.71 | 2.28 | 0.93 | 4.05 |
| Tmax, h | 2 | 1 | 1 | 2 | 4 | 4 |
| Cmax, ng/ml | 48.9 | 2090 | 397 | 875 | 647 | 55.3 |
| AUClast, h · ng/ml | 224 | 9448 | 2078 | 3935 | 3186 | 392 |
| AUCinf, h · ng/ml | 233 | 9469 | 2082 | 3938 | 3189 | 397 |
| MRTlast, h | 3.78 | 3.48 | 3.78 | 3.35 | 3.76 | 5.55 |
| $F_{AUClast}$, % | 23.9 | | | 62.2 | 39.6 | |

7-Hydroxy derivatives 1.1.2-1.14.2 are nanomolar inhibitors of influenza virus isolates. For example, the activity of inhibitors 1.8.2, 1.9.2, 1.13.2 and 1.14.2 against influenza A/California/2009 (H1N1) isolates in MDCK cell culture has a value of $EC_{50}$=2÷4 nM, which almost coincides with that of baloxavir (according to our sources, $EC_{50}$=2.4 nM). Inhibitor 1.3.2 against influenza isolates A/California/2009 (H1N1), A/Aichi/2/69 (H3N2), and A/Perth/265/2009 (H1N1pdm09) (H275Y) in MDCK cell culture even exceeds the activity of Baloxavir (BXA) under similar conditions (Table 3).

TABLE 3

Antiviral activities of novel inhibitor 1.2.2 and BXA against influenza A virus isolates in MDCK cell culture

| Drug | A/California/ 2009 (H1N1) | A/Aichi/2/68 (H3N2) | A/Perth/265/2009 (H1N1pdm09) (H275Y) |
|---|---|---|---|
| | | $EC_{50}$, nM | |
| 1.3.2 | <0.3 | 0.23 | 0.8 |
| BXA | 2.4 | 1.04 | 1.1 |

The subject of the present invention relates to the use of 7,8-difluoro-5,10-dihydrothieno[3,2-c][2]benzothiepin-10-ol (3), 7,8-difluoro-7,8-dihydrothieno[2,3-c][2]benzothiepin-10-ol (4), (3,4-difluorophenyl)(phenyl)methanol (5), (3,4-difluorophenyl)(2-methylsulfanylphenyl)methanol (6), diphenylmethanol (7), and bis(4-fluorophenyl)methanol (8) as intermediates for the synthesis of compounds of general formula 1.

The subject of this invention relates to the use of 7-benzyloxyderivatives 1.1.1-1.14.1 as intermediates for the synthesis of respective 7-hydroxy derivatives 1.1.2-1.14.2.

The subject of this invention relates to the use of 7-hydroxy derivatives 1.1.2-1.14.2 as intermediates for the synthesis of drugs 1.1.3-1.14.3 and 1.1.4-1.14.4.

The subject of this invention relates to the use of 7-hydroxy derivatives 1.1.2-1.14.2 or their stereoisomers, pharmaceutically acceptable salt, solvate, hydrate, and their crystalline or polycrystalline forms as influenza virus inhibitors.

The subject of this invention relates to the use of compounds 1.1.3-1.14.3 and 1.1.4-1.14.4 or their stereoisomers, pharmaceutically acceptable salts, solvates, hydrates, and their crystalline or polycrystalline forms as influenza virus pro-inhibitors (drugs).

The subject of this invention relates to the use of inhibitors 1.1.2-1.14.2 or drugs 1.1.3-1.14.3 and 1.1.4-1.14.4 or their stereoisomers, pharmaceutically acceptable salts, solvates, hydrates, and their crystalline or polycrystalline forms for the treatment and prevention of viral diseases.

The subject of this invention relates to an antiviral pharmaceutical composition containing a compound selected from the series 1.1.2-1.14.2, or the drug series 1.1.3-1.14.3 and 1.1.4-1.14.4, or the series of their stereoisomers, pharmaceutically acceptable salts, solvates, hydrates, and their crystalline or polycrystalline forms in a therapeutically effective amount for the treatment or prevention of viral diseases.

More preferable is an antiviral pharmaceutical composition comprising a compound selected from the series 1.1.2-1.14.2, or the drug series 1.1.3-1.14.3 and 1.1.4-1.14.4, or the series of their stereoisomers, pharmaceutically acceptable salts, solvates, hydrates, and their crystalline or polycrystalline forms in a therapeutically effective amount for the treatment or prevention of influenza.

The subject of this invention relates to a method for the treatment and/or prophylaxis of viral diseases, said method involving administration to the patient of a compound selected from the series 1.1.2-1.14.2, or the drug series 1.1.3-1.14.3 and 1.1.4-1.14.4, or the series of their stereoisomers, pharmaceutically acceptable salts, solvates, hydrates, and their crystalline or polycrystalline forms, or a pharmaceutical composition of this invention.

To treat the above-mentioned diseases, including influenza, in humans, the compounds of the present invention can be administered orally in the form of powder, granules, tablets, capsules, pills, liquids, etc. or parenterally in the form of injections, suppositories, percutaneous medication, inhaler, and the like. Effective doses of these compounds can be mixed with excipients suitable for the dosage form, such as fillers, binders, humidifiers, disintegrators and lubricants, if it is necessary for the production of pharmaceuticals. For injections, sterilization with a suitable carrier is to be performed.

Pharmaceutical compositions of this invention can be administered orally or parenterally. For oral administration, commonly used dosage forms such as tablets, granules, powder, and capsules can be produced conventionally. For parenteral administration, a suitable commonly used dosage form like injection can be used.

Effective doses for compounds of the present invention can be mixed with various pharmaceutical excipients suitable for the dosage form, such as fillers, binders, disintegrators, and lubricants, if it is necessary for the production of pharmaceutical compositions.

The dose of compounds of this invention depends on the condition of the disease, the route of administration, and the age or weight of the patient. The usual oral dose for adults is 0.1 to 100 mg/kg per day, preferably 1 to 20 mg/kg per day. The dosage of the pharmaceutical composition of this invention is preferably determined based on the age and weight of the patient, the type and severity of the disease, the route of administration, and the like. The usual oral dose for adults is in the range of 0.05 to 100 mg/kg per day, preferably 0.1 to 10 mg/kg per day. The parenteral dose for adults varies significantly depending on the route of administration, but is generally in the range of 0.005 to 10 mg/kg per day, preferably 0.01 to 1 mg/kg per day. The dose can be administered once a day or divided into several daily doses. The compound of the present invention can be used in combination with other medicinal products (hereinafter referred to as combined medicinal products) to increase the activity of the compound, reduce the dose of the compound, or the like.

For the treatment of influenza, the compound of this invention can be used in combination with a neuraminidase inhibitor (e.g., Oseltamivir, Zanamivir, Peramivir, AV-5080, Inabiru, and the like); an RNA-dependent RNA polymerase inhibitor (for example, Favipiravir); M2-protein inhibitor (for example, Amantadine); a PB2 cap-binding inhibitor, for example, VX-787); anti-NA antibody (for example, MHAA4549A); interferons (for example, Grippferon), interferon inducers (for example, Kagocel). Immune agonists are also possible (for example, nitazoxanide). In this case, the time of administration for the compound of this invention and the combination drug is not limited. They can be prescribed to patients in need thereof at the same time or at different times. In addition, the compound of this invention and the combination drug can be administered as two or more compositions regardless of each active ingredient or one composition containing each active ingredient.

The dose for combination drugs can be selected accordingly in relation to the clinical dose. The compounding ratio of the compounds of this invention to co-administered drugs can be appropriately selected depending on the patient to be treated, the route of administration, the disease to be treated, the symptoms, the combination of drugs, and the like. For administration in humans, for example, 1 part by weight of compounds of the present invention can be used in combination with 0.01-100 parts by weight of jointly administered drugs.

This invention is illustrated by the following drawings:

FIG. 1. Fragments of solvate packaging $1.2.1 \cdot C_2H_5OH$ (A) and $1.2.1 \cdot i\text{-}C_3H_7OH$ (B) obtained from X-ray crystal analysis using the Platon software.

FIG. 2. General view of one of two symmetrically independent solvate molecules $1.2.1 \cdot C_2H_5OH$ (A) and $1.2.1 \cdot i\text{-}C_3H_7OH$ (B), with atoms represented by ellipsoids of thermal vibrations p=50%. The solvate molecules of ethanol and isopropanol are not shown for clarity.

FIG. 3. General view of the molecule 1.9.1 with atoms represented by ellipsoids of thermal vibrations p=50% (A) and a version obtained using the Platon software (B).

BEST EMBODIMENT

The present invention is illustrated in more detail, without limiting thereof, by examples of the synthesis of compounds of general formula 1 and their tests.

General chemistry procedures. All chemicals and solvents were used as obtained from the suppliers, without further purification. Crude reaction mixtures were concentrated at low pressure by removing organic solvents on a rotary evaporator.

Nuclear magnetic resonance (NMR) spectra were recorded using a Bruker DPX-400 spectrometer at room temperature (rt) with tetramethylsilane as the internal standard. Chemical shifts (δ) are represented in parts per million (ppm), and signals are represented as s (singlet), d (doublet), t (triplet), q (quartet), m (multiplet), or br. s. (broad singlet).

High-resolution mass spectra (HRMS) were obtained using an Orbitrap Elite mass spectrometer (Thermo, Bremen, Germany) equipped with a HESI ion source.

High performance liquid chromatography (HPLC). The purity of the end compounds as determined by HPLC was more than 98%. The HPLC conditions for purity evaluation were: Shimadzu HPLC, XBridge C18, 4.6 mm×250 mm (3.5 μm); 0.1% TFA gradient in 5% acetonitrile/water (A) and 0.1% TFA acetonitrile (B); flow rate: 0.5 ml/min; collection time: 20 min; UV wavelength: 214 and 254 nm. The preparative HPLC system included two sets of Shimadzu LC-8A pumps, a Shimadzu SCL 10AVP controller, and a Shimadzu SPD 10AVP detector. We used a Reprosil-Pur C18-AQ column of 10 microns, 250 mm×20 mm. The mobile phase had a gradient of 0.1% TFA in water (A) and 0.1% TFA in acetonitrile (B). LC/MS was performed on a PE Sciex API 165 system using positive ion electrospray [M+H]+ and a Shimadzu HPLC system equipped with a Waters XBridge C18 3.5 μm (4.6 mm×150 mm) column. Diastereoisomers were divided into chiral HPLC Phenomenex Lux 5 u Cellulose-4, AXIA F, 250×30.00 mm. Flow rate: 25 ml/min. Detector: UV, 215 nm.

X-ray diffraction study of samples was performed on a Bruker APEX2 DUO diffractometer using CuKa radiation (graphite monochromator, ω-scanning). The structures were decoded by the direct method and refined by the least-squares technique in the anisotropic full-matrix approximation against $F^2_{hkl}$. The hydrogen atoms of the OH groups in the solvate molecules of ethanol and isopropanol were localized in difference Fourier syntheses, and the positions of the remaining atoms were calculated geometrically. All hydrogen atoms were refined in the isotropic approximation using the rider model. Calculations were performed using SHELXTL PLUS software [Sheldrick, G. M. *Acta Cryst.* 2008, A64: 112-122] and Olex2 [Dolomanov, O. V. et al. *J. Appl. Cryst.* 2009, 42, 339-341].

Example 1. Synthesis of 6,7-difluorothieno[3,2-c][2]benzothiepin-10(5H)-one (4.1) and 6,7-difluoro-5,10-dihydrothieno[3,2-c][2]benzothiepin-10-ol (3) (Scheme 1)

To a solution of 30 g (174.3 mmol, 1 eq.) of 3,4-difluoro-2-methylbenzoic acid (3.1) in 300 ml of methanol, 207 g (1.74 mol, 10 eq.) of thionyl chloride was added dropwise. The mixture was heated to a boil at reflux and kept for 17 hours. The reaction mass was evaporated on a rotary evaporator, the remainder was filled with water, the product was filtered and air-dried to give 26.4 g of 3,4-difluoro-2-methylbenzoic acid methyl ester (3.2) as a white crystalline powder: $^1H$ NMR (400 MHz, $CDCl_3$) δ 7.77-7.67 (m, 1H), 7.04 (dd, J=16.9, 8.9 Hz, 1H), 3.91 (s, 3H), 2.56 (d, J=2.7 Hz, 3H).

To a solution of 28.0 g (150.4 mmol, 1 eq.) of the resulting ester 3.2 in 650 ml of carbon tetrachloride, 67.0 g (376.0 mmol, 2.5 eq.) of N-bromosuccinimide was added at room temperature. The reaction mass was heated to a boil, and 360 mg of benzoyl peroxide (1.5 mmol, 0.01 eq.) was added in one portion. The reaction mass was stirred while boiling at reflux for 17 hours. The reaction mass was cooled to room temperature, the precipitate was filtered and washed with carbon tetrachloride. The filtrate was evaporated on a rotary evaporator, and the remainder was purified by column chromatography (silica gel, ethyl acetate:hexane 1:9) to give 39.9 g of 2-(bromomethyl)-3,4-difluoro-benzoic acid (3.3) methyl ester as a yellow oil, which crystallized when left to stand giving white crystals: $^1H$ NMR (400 MHz, $CDCl_3$) δ 7.87-7.77 (m, 1H), 7.19 (dd, J=16.8, 8.8 Hz, 1H), 5.02 (d, J=2.1 Hz, 2H), 3.96 (s, 3H).

To the suspension of 12.5 g (90.3 mmol, 1.5 eq.) of $K_2CO_3$ and 3.9 g (12.0 mmol, 0.2 eq.) of $Cs_2CO_3$ in 70 ml of DMF, 7.0 g (60.2 mmol, 1.1 eq.) of thiophene-3-thiol (3.4) was added, and the mixture was stirred at room temperature for 30 minutes. Then, 14.5 g (54.7 mmol, 1 eq.) of 2-(bromomethyl)-3,4-difluorobenzoic acid methyl ester (3.3) was added to the reaction mass and the mixture was stirred at room temperature for 17 hours. The mixture was evaporated to dryness on a rotary evaporator, and 150 ml of ethyl acetate and 250 ml of water were added to the remainder. The organic layer was separated and water was extracted with 150 ml of ethyl acetate. The combined organic extracts were washed with water, then with brine, dried over $Na_2SO_4$ and evaporated to dryness on a rotary evaporator. The product was purified by column chromatography (silica gel, hexane:ethyl acetate=1:0-100:1-50:1-10:1) to give 12.2 g of 3,4-difluoro-2-[(3-thienylthio)methyl]benzoic acid methyl ester (3.5) as a yellow oil: $^1H$ NMR (400 MHz, DMSO) δ 7.72-7.66 (m, 1H), 7.56 (dd, J=5.0, 3.0 Hz, 1H), 7.48-7.39 (m, 1H), 7.36 (dd, J=3.0, 1.2 Hz, 1H), 6.94 (dd, J=5.0, 1.2 Hz, 1H), 4.43 (d, J=1.6 Hz, 2H), 3.78 (s, 3H).

To a solution of 7.9 g (26.3 mmol, 1 eq.) of 3,4-difluoro-2-[(3-thienylthio)methyl]benzoic acid methyl ester (3.5) in 80 ml of methanol, a solution of 5.0 g (118.4 mmol, 4.5 eq.) of lithium hydroxide hydrate in 40 ml water was added. The mixture was stirred at room temperature for 17 hours and evaporated to dryness on a rotary evaporator. Then, 100 ml of water, 2N HCl to pH~1~3 were added to the residue and the suspension was stirred at room temperature for 30 min. The precipitate was filtered and air-dried to give 7 g of 3,4-difluoro-2-[(3-thienylthio)methyl]benzoic acid (3.6) as a white powder: $^1H$ NMR (400 MHz, DMSO) δ 13.36 (br.s, 1H), 7.78-7.71 (m, 1H), 7.56 (dd, J=5.0, 3.0 Hz, 1H), 7.47-7.34 (m, 2H), 6.98-6.92 (m, 1H), 4.48 (s, 2H).

To a solution of 1.0 g (3.5 mmol, 1 eq.) of 3,4-difluoro-2-[(3-thienylthio)methyl]benzoic acid (3.6) in 120 ml of benzene, 0.87 g (4.2 mmol, 1.2 eq.) of $PCl_5$ was added, and the mixture was stirred and boiled at reflux for 10 minutes, then cooled to room temperature. Argon (weak current) was passed through the reaction mass for 10 min. to remove hydrogen chloride. The reaction mass was cooled to 0° C., and 0.91 g (3.5 mmol, 1 eq.) of tin tetrachloride was added dropwase. The reaction mass was stirred and boiled at reflux for 10 minutes, then cooled. Then, 70 ml of ester was added to the reaction mass and the mixture was washed twice with 50 ml of 2N HCl, 50 ml of water and brine, respectively, dried over $Na_2SO_4$ and evaporated to dryness on a rotary evaporator. The product was isolated by column chromatography (silica gel, hexane:ethyl acetate=30:1-20:1) to give 3.9 g of 6,7-difluorothieno[3,2-C][2]benzothiepin-10(5H)-one (3.7) as a yellow powder: $^1H$ NMR (400 MHz, DMSO) δ 8.07 (d, J=5.3 Hz, 1H), 7.64-7.47 (m, 2H), 7.23 (d, J=5.2 Hz, 1H), 4.39 (s, 2H).

To a suspension of 3.9 g (14.5 mmol, 1 eq.) of 6,7-difluorothieno[3,2-c][2]benzothiepin-10(5H)-one (3.7) in 100 ml of methanol and 0.28 g (7.3 mmol, 0.5 eq.) of sodium borohydride were added, and the reaction mass was stirred at room temperature for 30 minutes. The reaction mass was evaporated on a rotary evaporator, and 100 ml of saturated $NaHCO_3$ solution in water was added to the remainder. The product was filtered, washed with water, and air-dried to give 3.9 g of 6,7-difluoro-5,10-dihydrothieno[3,2-c][2]benzothiepin-10-ol (3) as a yellowish powder: $^1H$ NMR (400 MHz, DMSO) δ 7.47-7.26 (m, 3H), 6.84-6.63 (m, 2H), 6.27 (s, 1H), 4.59 (d, J=14.2 Hz, 1H), 4.42 (d, J=14.3 Hz, 1H).

Example 2. 7,8-Difluoro-4,9-dihydrothieno[2,3-c][2]benzothiepin-4-ol (4) (Scheme 2)

To a suspension of 8.9 g (64.5 mmol) of $K_2CO_3$ and 2.8 g (8.6 mmol) of $Cs_2CO_3$ in 50 ml of DMF, 5.0 g (43.0 mmol) of thiophene-2-thiol (4.1) was added, and the mixture was stirred at room temperature for 30 min. Then, 11.4 g (43.0 mmol) of 2-(bromomethyl)-3,4-difluoropbenzoic acid methyl ester (3.3) was added, and the mixture was stirred at room temperature for 17 hours. The resulting mixture was evaporated to dryness on a rotary evaporator, 150 ml of ethyl acetate and 250 ml of water were added to the remainder. The organic layer was separated and the aqueous layer was extracted with 150 ml of ethyl acetate. The combined organic extracts were washed with water, then with brine, dried over $Na_2SO_4$ and evaporated to dryness on a rotary evaporator. The product was purified by column chromatography (silica gel, dichloromethane-hexane 1:4) to give 9.2 g of 3,4-difluoro-2-[(2-thienylthio)methyl]benzoic acid methyl ester (4.2) as a yellow oil. $^1H$ NMR (400 MHz, DMSO) δ 7.76-7.70 (m, 1H), 7.64 (dd, J=5.3, 1.2 Hz, 1H), 7.47 (dd, J=18.1, 8.6 Hz, 1H), 7.00 (dd, J=5.3, 3.6 Hz, 1H), 6.97-6.93 (m, 1H), 4.41 (s, 2H), 3.77 (s, 3H).

To a solution of 9.2 g (30.6 mmol) of 3,4-difluoro-2-[(2-thienylthio)methyl]-benzoic acid methyl ester (4.2) in 50 ml of methanol, a solution of 2.6 g (45.9 mmol) of KOH in 50 ml of water was added. The mixture was stirred at room temperature for 17 hours and then stripped of methanol under reduced pressure. The aqueous residue was extracted twice with 50-ml portions of ether, and 2N HCl was acidified to pH~1-3. The precipitate was stirred at room temperature for 30 min. The sediment was filtered out and air-dried to give 8.4 g of 3,4-difluoro-2-[(2-thienylthio)methyl]benzoic acid (4.3) as a white powder. $^1H$ NMR (400 MHz, DMSO) δ 13.36 (s, 1H), 7.81-7.74 (m, 1H), 7.63 (dd, J=5.2, 1.2 Hz, 1H), 7.43 (dd, J=17.8, 8.7 Hz, 1H), 7.03-6.94 (m, 2H), 4.44 (s, 2H).

To a solution of 4.2 g (4.7 mmol) of 3,4-difluoro-2-[(2-thienylthio)methyl]benzoic acid (4.3) in 70 ml of benzene, 3.7 g (17.6 mmol) of $PCl_5$ was added, and the mixture was stirred and boiled at reflux for 10 min, then cooled to room temperature. To remove hydrogen chloride, argon (weak current) was passed through the reaction mass for 10 min. The reaction mass was cooled in an ice-water bath to 0° C., and 3.8 g (14.7 mmol, 1 eq.) of tin tetrachloride was added dropwise. The reaction mass was stirred and boiled at reflux for 10 min, then cooled to room temperature. Ether (70 ml) was then added, and the reaction mass was washed twice with 50-ml portions of 2N HCl, 50 ml of water, brine, dried over $Na_2SO_4$, and evaporated to dryness on a rotary evaporator. The product was isolated by column chromatography (silica gel, hexane:ethyl acetate 20:1) to give 1.8 g of 7,8-difluorothieno[2,3-c][2]benzothiepin-4(9H)-one (4.4) as a yellow powder. $^1H$ NMR (400 MHz, DMSO) δ 7.62-7.45 (m, 4H), 4.49 (s, 2H).

To a suspension of 1.8 g (6.7 mmol) of 7,8-difluorothieno [2,3-c][2]benzothiepin-4(9H)-one (4.4) in 50 ml of methanol, 0.25 g (6.7 mmol) of sodium borohydride was added, and the reaction mass was stirred at room temperature for 30 min. The reaction mass was evaporated on a rotary evaporator, the remainder was suspended in 50 ml of methylene chloride and washed with 50 ml of a saturated $NaHCO_3$ solution. The methylene solution was dried over $Na_2SO_4$ and evaporated to dryness. The residue in the flask crystallized. The product was washed with water and air-dried to give 1.7 g of 7,8-difluoro-4,9-dihydrothieno[2,3-c][2]benzothiepin-4-ol (4) as a yellowish powder. $^1H$ NMR (400 MHz, DMSO) δ 7.35-7.25 (m, 2H), 7.25-7.18 (m, 1H), 7.07 (d, J=4.7 Hz, 1H), 6.27 (d, J=4.0 Hz, 1H), 5.96 (d, J=3.9 Hz, 1H).

Example 3. (3,4-Difluorophenyl)(phenyl)methanol (5) was prepared similarly to the synthesis of alcohols 3 and 4 from corresponding ketones 3.7 and 4.4. (3,4-Difluorophenyl)(phenyl)methanol (5): LC-MS (ESI, 20 min), 221 $(M+H)^+$; $^1H$ NMR (DMSO-$d_6$, 400 MHz) δ 7.29-7.42 (m, 6H), 7.17-7.24 (m, 2H), 6.06 (d, J=4.0 Hz, 1H), 5.71 (d, J=4.0 Hz, 1H).

Example 4. (3,4-Difluorophenyl)(2-methylsulfanylphenyl)methanol (6)

To a suspension of 11.0 g (79.4 mmol, 1.5 eq.) of $K_2CO_3$ and 3.5 g (10.6 mmol, 0.2 eq.) of $Cs_2CO_3$ in 50 ml of DMF, 10.0 g (52.9 mmol, 1 eq.) of 1-bromo-2-thiophenol (6.1) was added, and the reaction mass was stirred at room temperature for 30 min. Then, 11.3 g (79.4 mmol, 1.5 eq.) of iodomethane was added and the mixture was stirred at room temperature for 1 hour. The mixture was poured into 200 ml of water, extracted with diethyl ether, the combined organic phases were washed with water, then with brine, and dried over $Na_2SO_4$. The solvent was evaporated to dryness on a rotary evaporator, and the product was used in the next stage without additional purification. The yield was 10.4 g (97%) of 1-bromo-2-methylsulfanylbenzene (6.2) as a yellow oil: $^1H$ NMR (400 MHz, $CDCl_3$) δ 7.54 (dd, J=7.9, 1.2 Hz, 1H), 7.36-7.28 (m, 1H), 7.15 (d, J=7.9 Hz, 1H), 7.02 (td, J=7.8, 1.4 Hz, 1H), 2.49 (s, 3H).

To a solution of 18.7 g (118.3 mmol, 1 eq.) of 3,4-difluoropbenzoic acid (6.4) in 374 ml of methylene chloride, 20.1 g (124.2 mmol, 1.05 eq.) of CDI was slowly added, and the mixture was stirred at room temperature for 15 minutes until $CO_2$ stopped evolving. Then, 12.7 g (130.1 mmol, 1.1 eq.) of N,O-dimethylhydroxylamine hydrochloride was added, and the reaction mixture was stirred at room temperature for 17 h. The mixture was diluted with 400 ml of water, the layers were separated, and the water layer was twice extracted with 100-ml portions of methylene chloride. The combined organic layers were washed with 200 ml of water, 100 ml of brine, dried over $Na_2SO_4$ and evaporated on a rotary evaporator to give 12 g (50%) of 3,4-difluoro-N-methoxy-N-methylbenzamide (6.5) as a colorless oil:

$^1H$ NMR (400 MHz, $CDCl_3$) δ 7.66-7.57 (m, 1H), 7.57-7.49 (m, 1H), 7.20 (dd, J=18.1, 8.3 Hz, 1H), 3.56 (s, 3H), 3.37 (s, 3H).

To a suspension of 1.49 g (61.4 mmol, 1.2 eq.) of Mg in 60 ml of THF, 10.4 g (51.2 mmol, 1 eq.) of 1-bromo-2-(methylsulfanyl)benzene (6.2) was added, and the mixture was stirred at room temperature for 2 h to give a solution of [2-(methylsulfanyl)phenyl]magnesium bromide (6.3) in THF.

To a cooled to (−78°) C (acetone, dry ice) solution of 10.3 g (51.2 mmol, 1 eq.) of 3,4-difluoro-N-methoxy-N-methylbenzamide (6.5) in 60 ml of THF, a solution of [2-(methylsulfanyl)phenyl]magnesium bromide (6.3) in THF was added dropwise while maintaining the temperature at (−78)-(−60°) C. The mixture was stirred at (−70°) C for 15 min, then heated to room temperature and stirred for 17 hours. The reaction mass was cooled to 0° C., 200 ml of 1N HCl was added, and the mixture was stirred in an ice bath for 15 min. Then, 50 ml of ethyl acetate and 100 ml of water were added to the mixture, the organic layer was separated, and the aqueous layer was twice extracted with 100-ml portions of ethyl acetate. The combined organic extract was twice washed with 50-ml portions of water, then with brine, dried over $Na_2SO_4$, and evaporated to dryness on a rotary evaporator. The product was purified by column chromatography (silica gel, ethyl acetate:hexane=30:1-20:1) to give 3.6 g of (3,4-difluorophenyl)(2-methylsulfanylphenyl)methanone (6.6) as a colorless oil: $^1H$ NMR (400 MHz, $CDCl_3$) δ 7.71-7.64 (m, 1H), 7.58-7.47 (m, 2H), 7.46-7.41 (m, 1H), 7.39-7.34 (m, 1H), 7.28-7.22 (m, 2H), 2.44 (s, 3H).

To a solution of 3.6 g (13.6 mmol, 1 eq.) of (3,4-difluorophenyl)(2-methylsulfanylphenyl)methanone (6.6) in 36 ml of methanol, 0.26 g (6.8 mmol, 0.5 eq.) of $NaBH_4$ was added, and the reaction mass was stirred at room temperature for 30 min and then evaporated on a rotary evaporator; 10 ml of 2N HCl was added to the remainder, and the mixture was stirred at room temperature for 5 min. A saturated $NaHCO_3$ solution (100 ml) was added portionwise, and the organic product was thrice extracted with 60-ml portions of ethyl acetate. The combined extract was washed with brine, dried over $Na_2SO_4$ and evaporated to dryness on a rotary evaporator. The product was purified by column chromatography (silica gel, hexane:ethyl acetate=30:1—15:1—9:1—7:1—5:1) to give 2.9 g of (3,4-difluorophenyl)(2-methylsulfanylphenyl)methanol (77%) as a colorless oil (6): $^1H$ NMR (400 MHz, DMSO) δ 7.51 (d, J=7.5 Hz, 1H), 7.38-7.26 (m, 4H), 7.23-7.17 (m, 1H), 7.13-7.07 (m, 1H), 6.10 (d, J=4.3 Hz, 1H), 5.97 (d, J=4.3 Hz, 1H), 2.44 (s, 3H).

Example 5. (12aR)-7-(Benzyloxy)-12-(5,10-dihydro[3,2-c][2]benzothiepin-10-yl)-3,4,12,12a-tetrahydro-1H-[1,4]oxazino[3,4-c]pyrido[2,1-c][1,2,4]triazine-6,8-dione 1.1.1 and its diastereomers 1.2.1, 1.3.1

To a mixture of 3.3 g (10.1 mmol, 1 eq.) of 7-(benzyloxy)-3,4,12,12a-tetrahydro-1H-[1,4]oxazino [3,4-c]pyrido[2,1-f][1,2,4]triazine-6,8-dione (2) and 4.1 g (15.2 mmol, 1.5 eq.) of 6,7-difluoro-5,10-dihydrothieno[3,2-c][2]benzothiepin-10-ol (3), 64.3 g (101 mmol, 10 eq.) of a 50% $T_3R$ solution in ethyl acetate was added. The reaction mass was stirred at room temperature for 5 days, poured into a mixture of 200 ml of saturated $NaHCO_3$ solution and 200 ml of ethyl acetate. The aqueous solution was separated, and the ethyl acetate layer was again washed with a saturated $NaHCO_3$ solution, then with brine, dried over $Na_2SO_4$, and evaporated on a rotary evaporator. The product was purified by column chromatography (EtOAc) to yield compound 1.1.1 as a white powder (5.7 g, 97%). The resulting mixture of diastereomers was recrystallized from 170 ml of ethyl acetate. The precipitate was filtered and washed on a filter with ethyl acetate to yield diastereomer 1.3.1 as a white powder (1.46 g, 25%). The filtrate was evaporated to dryness on a rotary evaporator, the remainder was separated on a chiral HPLC to yield diastereomer 1.2.1, which was the first to come out of the column, and diastomer 1.3.1, which was the second to come out of the column. In addition, 2.8 g of diastomer 1.2.1 was recrystallized from 100 ml of isopropanol. The absolute configuration of diastomers 1.2.1 and 1.3.1 was established based on the XRD data (Table 4) for rhombic solvates (FIGS. 1 and 2) 1.2.1·$C_2H_5$ and 1.2.1·i-$C_3H_7$ (in the ratios 4:3 and 8:3, respectively) resulted from the crystallization of diastomer 1.2.1 from ethanol and isopropanol.

TABLE 4

Basic crystallographic data and refinement parameters for 1.2.1 · $C_2H_5$ and 1.2.1 · i-$C_3H_7$.

| Parameters | 1.2.1 · $C_2H_5$ | 1.2.1 · i-$C_3H_7$ |
|---|---|---|
| Molecular formula | $C_{122}H_{110}F_8N_{12}O_{19}S_8$ | $C_{241}H_{208}F_{16}N_{24}O_{35}S_{16}$ |
| Molecular mass | 2456.69 | 4817.26 |
| T, K | 120 | 120 |
| Crystal system | Rhombic | Rhombic |
| Space group | $P2_12_12$ | $P2_12_12$ |
| Z | 2 | 1 |
| a, Å | 15.2405 (4) | 15.2647 (3) |
| b, Å | 33.4723 (8) | 33.3600 (7) |
| c, Å | 11.2776 (3) | 11.4164 (3) |
| α, ° | 90.00 | 90.00 |
| β, ° | 90.00 | 90.00 |
| γ, ° | 90.00 | 90.00 |
| V, $Å^3$ | 5753.1 (3) | 5813.6 (2) |
| $d_{выч}$, g × $cm^{-3}$ | 1.418 | 1.376 |
| μ, $cm^{-1}$ | 21.77 | 21.35 |
| F (000) | 2556 | 2502 |
| $2\theta_{max}$, ° | 135 | 135 |
| Number of measured reflections | 76014 | 82664 |
| Number of independent reflections | 10279 | 10421 |
| Number of reflections c I > 2 σ(I) | 9918 | 9852 |
| Number of refined parameters | 779 | 760 |
| R1 | 0.0347 | 0.0522 |
| wR2 | 0.0904 | 0.1513 |
| GOF | 1.077 | 1.107 |
| Residual electron density, e × $Å^{-3}$ ($d_{max}/d_{min}$) | 0.692/−0.413 | 0.810/−0.390 |

Diastereomer 1.2.1: LC MS, m/z 580 (M+1); $^1H$ NMR (400 MHz, DMSO) δ 7.76 (d, J=5.3 Hz, 1H), 7.56 (d, J=7.4 Hz, 2H), 7.40-7.29 (m, 3H), 7.21-7.11 (m, 1H), 7.03 (d, J=7.7 Hz, 1H), 6.91 (d, J=5.4 Hz, 1H), 6.83-6.75 (m, 1H), 5.76-5.65 (m, 2H), 5.34-5.22 (m, 2H), 5.15 (d, J=11.0 Hz, 1H), 4.56-4.48 (m, 2H), 4.13 (d, J=14.4 Hz, 1H), 3.99-3.92 (m, 1H), 3.73-3.66 (m, 1H), 3.39 (t, J=10.3 Hz, 1H), 2.96-2.86 (m, 1H), 1.04 (d, J=6.0 Hz, 1H).

Diastereomer 1.3.1: LC MS, m/z 580 (M+1); $^1H$ NMR (400 MHz, DMSO) 7.57 (d, J=7.0 Hz, 2H), 7.51-7.29 (m, 6H), 7.23 (d, J=7.7 Hz, 1H), 6.77 (d, J=5.4 Hz, 1H), 5.88-5.80 (m, 2H), 5.49-5.34 (m, 1H), 5.25 (d, J=10.7 Hz, 1H), 5.14 (d, J=10.8 Hz, 1H), 4.50-4.40 (m, 1H), 4.35 (dd, J=9.9, 2.9 Hz, 1H), 4.07 (d, J=9.8 Hz, 1H), 3.85 (dd, J=10.7, 2.8 Hz, 1H), 3.70-3.59 (m, 1H), 3.36 (t, J=10.3 Hz, 1H), 3.28-3.19 (m, 1H), 2.99-2.81 (m, 1H).

Example 6. (12aR)-7-Hydroxy-12-(5,10-dihydro[3,2-c][2]benzothiepin-10-yl)-3,4,12,12a-tetrahydro-1H-[1,4]oxazino[3,4-c]pyrido[2,1-c][1,2,4]triazine-6,8-dione 1.1.2 and its diastereomers 1.2.2 and 1.3.2

To a solution of 0.173 mol (1 eq.) of (12aR)-7-(benzyloxy)-12-(5,10-dihydro[3,2-c][2]benzothiepin-10-yl)-3,4,12,12a-tetrahydro-1H-[1,4]oxazino[3,4-c]pyrido[2,1-c][1,2,4]triazine-6,8-dione (1.1.1) or its diastereomers 1.2.1 or 1.3.1 in 15 ml of dimethylacetamide, 36 mg (0.863 mmol, 5 eq.) of LiCl was added, and the reaction mass was heated to 80° C. and stirred for 2 hours. The reaction mass was then evaporated to dryness on a rotary evaporator, 50 ml of aqueous 0.5N HCl was added to the remainder, and the product was thrice extracted with 30-ml portions of ethyl acetate. The combined extract was washed with brine, dried over $Na_2SO_4$, and evaporated to dryness on a rotary evaporator. The residue was purified by HPLC to yield inhibitor 1.1.2 (LC MS, m/z 454 (M+1)) or its diastereomers 1.1.2, 1.3.2 (LC MS, m/z 454 (M+1)). According to NMR data, the inhibitor 1.1.2 is a mixture of diastereomers 1.2.2 and 1.3.2 in the ratio 65:35.

Diastereomer 1.2.2: LC MS, m/z 454 (M+1); $^1H$ NMR (400 MHz, DMSO) δ 7.53-7.37 (m, 3H), 7.14 (d, J=7.8 Hz, 1H), 6.77 (d, J=5.3 Hz, 1H), 5.86 (s, 1H), 5.69 (d, J=7.7 Hz, 1H), 5.41 (d, J=14.1 Hz, 1H), 4.42 (d, J=10.6 Hz, 2H), 4.09 (d, J=14.2 Hz, 1H), 3.90-3.81 (m, 1H), 3.70-3.56 (m, 2H), 3.46-3.39 (m, 2H), 3.00 (s, 1H).

Diastereomer 1.3.2: LC MS, m/z 454 (M+1); $^1H$ NMR (400 MHz, DMSO) δ 7.76 (d, J=5.3 Hz, 1H), 7.20 (dd, J=18.5, 8.3 Hz, 1H), 7.05-6.87 (m, 3H), 5.84 (s, 1H), 5.56 (d, J=7.7 Hz, 1H), 5.28 (d, J=14.9 Hz, 1H), 4.57 (dd, J=9.8, 2.8 Hz, 1H), 4.49 (d, J=11.8 Hz, 1H), 4.13 (d, J=14.5 Hz, 1H), 4.01-3.93 (m, 1H), 3.76-3.68 (m, 1H), 3.62 (t, J=10.3 Hz, 1H), 3.49-3.39 (m, 2H), 3.05-2.94 (m, 1H);

Example 7. ({(12aR)-12-[(10S)-5,10-Dihydrothieno[3,2-c][2]benzothiepin-10-yl]-4,8-dioxo-3,4,6,8,12,12a-hexahydro-1H-[1,4]oxazino[3,4-c]pyrido[2,1-f][1,2,4]triazine-6-yl}oxy)methyl methyl carbonate 1.1.4 and its diastereoisomers 1.2.4, 1.3.4

To a suspension of 0.5 mmol of compound 1.1.2 or its diastereomer 1.2.2, 1.3.2 in 1 ml of dimethylacetamide, 93 mg (0.75 mmol) of chloromethyl methyl carbonate, 137 mg (1.0 mmol) of potassium carbonate, and 82 mg (0.5 mol) of potassium iodide were added, and the reaction mass was heated to 60° C. and stirred for 48 hours. The reaction mass was evaporated to dryness on a rotary evaporator, 10 ml of 0.5N HCl was added to the residue, and the product was thrice extracted with 30-ml portions of EtOAc. The combined extract was washed with 30 ml of a saturated aqueous $NaHCO_3$ solution, dried over $Na_2SO_4$, and evaporated to dryness on a rotary evaporator. The residue was purified by HPLC to give a prodrug 1.1.4 (LC MS, m/z 578 (M+1)) or its diastereoisomers 1.2.4 (LC MS, m/z 578 (M+1)), 1.3.4 (LC MS, m/z 578 (M+1)).

Example 8. (12aR)-12-[(10S)-5,10-Dihydrothieno[3,2-c][2]benzothiepin-10-yl]-4,8-dioxo-3,4,6,8,12,12a-hexahydro-1H-[1,4]oxazino[3,4-c]pyrido[2,1-f][1,2,4]triazine-6-yl methyl carbonate 1.1.3 and its diastereoisomers 1.2.3, 1.3.3.

Prodrugs 1.1.3 (LC MS, m/z 548 (M+1)), 1.2.3 (LC MS, m/z 548 (M+1)) and 1.3.3 (LC MS, m/z 548 (M+1)) were prepared similarly to those in Example 6 using chloroformic acid methyl ester for carbomethoxylation of compounds 1.1.2, 1.2.2, and 1.3.2, respectively.

Example 9. (12aR)-7-(Benzyloxy)-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4]triazine-6,8-dione 1.4.1 and its diastereomers 1.5.1, 1.6.1

To a solution of 4.6 mmol of 7,8-difluoro-4,9-dihydrothieno[2,3-c][2]benzothiepin-4-ol (4) in 50 ml of pyridine, 0.52 g (4.6 mmol) of mesyl chloride was added dropwise at 0° C., and the resulting mixture was stirred at room temperature for 24 h. Then, 7-(benzyloxy)-3,4,12,12a-tetrahydro-1H-[1,4]oxazino[3,4-c]pyrido[2,1-f][1,2,4]triazine-6,8-dione (2) was added, and the mixture was stirred for another 24 h at 70° C. Pyridine was evaporated at reduced pressure; the residue was dissolved in 100 ml of methylene chloride, washed with 50 ml of water, dried over sodium sulfate, and evaporated. The resulting product was purified by column chromatography on silica gel with pure ethyl acetate to give (12aR)-7-(benzyloxy)-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4]triazine-6,8-dione 1.4.1 consisting of diastereomers 1.5.1, 1.6.1, which were isolated on a preparative chiral column Phenomenex Lux 5 u Cellulose-4, AXIA F, 250×30.00 mm. Flow rate: 25 ml/min; detector: UV, 254 nm; constant mobile phase composition: acetonitrile-isopropanol 80:20.

(12aR)-7-(Benzyloxy)-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4]triazine-6,8-dione (1.4.1: LC MS m/z 580 (M+1); $^1$H NMR (400 MHz, DMSO) δ 7.61-7.51 (m, 2.6H), 7.48-7.29 (m, 3.8H), 7.25 (d, J=7.7 Hz, 0.4H), 7.20-7.09 (m, 1H), 7.02 (dd, J=12.0, 6.5 Hz, 1.2H), 6.76-6.67 (m, 0.6H), 6.26 (d, J=5.2 Hz, 0.4H), 5.83 (s, 0.4H), 5.73-5.66 (m, 1.2H), 5.48 (d, J=14.6 Hz, 0.4H), 5.35-5.26 (m, 1.6H), 5.18-5.10 (m, 1H), 4.54-4.41 (m, 1H), 4.36-4.29 (m, 1H), 4.24 (d, J=14.5 Hz, 0.6H), 4.18 (d, J=14.3 Hz, 0.4H), 3.94 (d, J=7.6 Hz, 0.6H), 3.84 (d, J=7.8 Hz, 0.4H), 3.72-3.61 (m, 1H), 3.42-3.32 (m, 1.4H), 3.29-3.20 (m, 1H), 2.91 (t, J=11.0 Hz, 0.4H), 2.83 (t, J=10.9 Hz, 0.6H).

Diastereomer 1.5.1: IC MS m/z 580 (M+1); $^1$H NMR (400 MHz, DMSO) δ 7.54 (t, J=5.5 Hz, 3H), 7.38 (t, J=7.2 Hz, 2H), 7.33 (t, J=7.2 Hz, 1H), 7.22-7.11 (m, 1H), 7.02 (dd, J=12.0, 6.5 Hz, 2H), 6.76-6.67 (m, 1H), 5.73-5.66 (m, 2H), 5.35-5.26 (m, 2H), 5.14 (d, J=10.9 Hz, 1H), 4.49 (d, J=11.8 Hz, 1H), 4.32 (d, J=6.9 Hz, 1H), 4.24 (d, J=14.5 Hz, 1H), 3.94 (d, J=7.6 Hz, 1H), 3.68 (d, J=8.8 Hz, 1H), 3.39-3.34 (m, 1H), 3.29-3.21 (m, 1H), 2.83 (t, J=10.9 Hz, 1H).

Diastereomer 1.6.1: IC MS m/z 580 (M+1); $^1$H NMR (400 MHz, DMSO) δ 7.57 (d, J=6.9 Hz, 2H), 7.48-7.29 (m, 5H), 7.25 (d, J=7.7 Hz, 1H), 7.11 (d, J=5.2 Hz, 1H), 6.26 (d, J=5.2 Hz, 1H), 5.83 (s, 1H), 5.48 (d, J=14.6 Hz, 1H), 5.29 (d, J=11.0 Hz, 1H), 5.12 (d, J=10.9 Hz, 1H), 4.46 (d, J=12.0 Hz, 1H), 4.33 (d, J=7.0 Hz, 1H), 4.18 (d, J=14.3 Hz, 1H), 3.84 (d, J=7.8 Hz, 1H), 3.65 (d, J=11.2 Hz, 1H), 3.42-3.34 (m, 2H), 3.25 (t, J=10.7 Hz, 1H), 2.91 (t, J=11.0 Hz, 1H).

Example 10. 7-Hydroxy-(12aR)-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4]triazine-6,8-dione 1.4.2 and its diastereomers 1.5.2 and 1.6.2

To a solution of 0.14 mmol of 7-benzyloxy derivative 1.4.2, 1.5.2 or 1.6.2 in 5 ml of dimethylacetamide, 9 mg (0.70 mmol) of LiCl was added, and the reaction mass was heated to 80° C. and stirred for 3 hours. The reaction mass was evaporated to dryness on a rotary evaporator, and the residue was purified by HPLC to give a respective product 1.4.2, 1.5.2 or 1.6.2.

7-Hydroxy-(12aR)-12-(7,8-difluoro-4,9-dihydrothieno[2,3-c][2]benzothiepin-4-yl)-3,4,12,12a-tetrahydro-1H-[1,4]oxazino[3,4-c]pyrido[2,1-f][1,2,4]triazine-6,8-diones 1.4.2: LC MS, m/z 454 (M+1); $^1$H NMR (400 MHz, DMSO) δ 7.53 (d, J=5.2 Hz, 0.5H), 7.44 (dd, J=18.2, 8.4 Hz, 0.5H), 7.38-7.31 (m, 0.5H), 7.27-7.13 (m, 1.5H), 7.03 (d, J=5.3 Hz, 0.5H), 6.97 (d, J=7.7 Hz, 0.5H), 6.92-6.85 (m, 0.5H), 6.42 (d, J=5.3 Hz, 0.5H), 5.87 (s, 0.5H), 5.80 (s, 0.5H), 5.69 (d, J=7.6 Hz, 0.5H), 5.56 (d, J=7.7 Hz, 0.5H), 5.48 (d, J=13.5 Hz, 0.5H), 5.33 (d, J=14.4 Hz, 0.5H), 4.53-4.35 (m, 2H), 4.30-4.14 (m, 1H), 3.96 (dd, J=10.6, 2.7 Hz, 0.5H), 3.90-3.81 (m, 0.5H), 3.69 (t, J=12.4 Hz, 1H), 3.59 (t, J=10.3 Hz, 1H), 3.46-3.41 (m, 1H), 3.08-2.97 (m, 0.5H), 2.91 (t, J=11.0 Hz, 0.5H).

Diastereomer 1.5.2: LC MS, m/z 454 (M+1); $^1$H NMR (400 MHz, DMSO) δ 11.80 (br.s, 1H), 7.43 (dd, J=18.2, 8.6 Hz, 1H), 7.38-7.29 (m, 1H), 7.17 (t, J=6.3 Hz, 2H), 6.42 (d, J=5.2 Hz, 1H), 5.87 (s, 1H), 5.69 (d, J=7.6 Hz, 1H), 5.49 (d, J=14.7 Hz, 1H), 4.55-4.33 (m, 2H), 4.19 (d, J=14.4 Hz, 1H), 3.86 (d, J=8.0 Hz, 1H), 3.67 (d, J=9.2 Hz, 1H), 3.59 (t, J=10.4 Hz, 1H), 3.40 (t, J=10.5 Hz, 1H), 3.03 (t, J=11.0 Hz, 1H).

Diastereomer 1.6.2: LC MS, m/z 454 (M+1); $^1$H NMR (400 MHz, DMSO) δ 11.77 (s, 1H), 7.53 (d, J=5.1 Hz, 1H), 7.21 (dd, J=17.9, 8.6 Hz, 1H), 7.03 (d, J=5.2 Hz, 1H), 6.97 (d, J=7.6 Hz, 1H), 6.93-6.82 (m, 1H), 5.80 (s, 1H), 5.56 (d, J=7.6 Hz, 1H), 5.33 (d, J=14.6 Hz, 1H), 4.48 (d, J=12.6 Hz, 1H), 4.39 (d, J=7.6 Hz, 1H), 4.25 (d, J=14.5 Hz, 1H), 3.96 (d, J=8.6 Hz, 1H), 3.71 (d, J=9.3 Hz, 1H), 3.59 (t, J=10.2 Hz, 1H), 3.42 (t, J=10.8 Hz, 1H), 2.91 (t, J=11.2 Hz, 1H).

Example 11. ({(12aR)-12-[(4S)-7,8-Difluoro-4,9-dihydrothieno[2,3-c][2]benzothiepin-4-yl]-6,8-dioxo-3,4,6,8,12,12a-hexahydro-1H-[1,4]oxazino[3,4-c]pyrido[2,1-][1,2,4]triazin-7-yl}oxy) methyl carbonates 1.5.4 and ({(12aR)-12-[(4R)-7,8-difluoro-4,9-dihydrothieno[2,3-c][2]benzothiepin-4-yl]-6,8-dioxo-3,4,6,8,12,12a-hexahydro-1H-[1,4]oxazino[3,4-c]pyrido[2,1-f][1,2,4]triazin-7-yl}oxy) methyl carbonate 1.6.4

Prodrugs 1.5.4 and 1.6.4 were prepared under conditions similar to those described in Example 6 starting from respective diastereomers 1.5.2 and 1.6.2. Prodrug 1.5.4: LC MS, m/z 578 (M+1). Prodrug 1.6.4: LC MS, m/z 578 (M+1).

Example 12. (12aR)-7-(Benzyloxy)-12-[(3,4-difluorophenyl)(phenyl)methyl]-3,4,12,12a-tetrahydro-1H-[1,4]oxazino[3,4-c]pyrido[2,1-f][1,2,4]triazine-6,8-dione 1.7.1 and its diastereomers 1.8.1, 1.9.1

To a mixture of 900 mg (2.7 mmol) of (12aR)-7-(benzyloxy)-3,4,12,12a-tetrahydro-1H-[1,4]oxazino[3,4-c]pyrido[2,1-f] [1,2,4]triazine-6,8-dione (2) and 605 mg (2.7 mmol) of (3,4-difluorophenyl)(phenyl)methanol (5) in 17.5 g (27.0 mmol) of 50% $T_3R$ in ethyl acetate, 528 mg (5.4 mmol) of methanesulfonic acid was added, and the mixture was stirred at 70° C. for 16 h. The reaction mass was cooled to room temperature, then 50 ml of ethyl acetate was added, and the mixture was washed with 50 ml of saturated $NaHCO_3$ solution, dried over $Na_2SO_4$ and evaporated to dryness on a rotary evaporator. The resulting product was purified by column chromatography on silica gel with pure ethyl acetate, and respective fractions were evaporated to give 240 mg of the product (1.7.1): LC MS (20 min): Rt=15.53 (220 nm), m/z 530 (M+1) consisting of (12aR)-7-(benzyloxy)-12-[(R)-(3,4-difluorophenyl)(phenyl)methyl]-3,4,12,12a-tetrahydro-1H-[1,4]oxazino[3,4-c]pyrido[2,1-f][1,2,4]triazine-6,8-dione (1.8.1) and (12aR)-7-(benzyloxy)-12-[(S)-(3,4-difluorophenyl)(phenyl)methyl]-3,4,12,12a-tetrahydro-1H-[1,4]oxazino[3,4-c]pyrido[2,1-f][1,2,4]triazine-6,8-dione (1.9.1), which were separated on a preparative chiral column Phenomenex Lux 5 u Cellulose-4, AXIA F, 250×

30.00 mm. Flow rate: 25 ml/min; detector: UV, 254 nm; constant mobile phase composition: acetonitrile-isopropanol 80:20.

Diastereomer 1.8.1: $^1$H NMR (400 MHz, $CDCl_3$) δ 7.61 (d, J=6.6 Hz, 2H), 7.40-7.33 (m, 4H), 7.25-7.17 (m, 3H), 7.12 (t, J=7.6 Hz, 2H), 6.93 (d, J=7.5 Hz, 2H), 6.73 (d, J=7.7 Hz, 1H), 5.75 (d, J=7.9 Hz, 1H), 5.59 (d, J=10.7 Hz, 1H), 5.45 (d, J=10.8 Hz, 1H), 5.39 (s, 1H), 4.65 (d, J=13.8 Hz, 1H), 4.58-4.50 (m, 1H), 3.97 (d, J=10.4 Hz, 1H), 3.73 (d, J=8.9 Hz, 1H), 3.37-3.22 (m, 2H), 2.96 (t, J=10.9 Hz, 1H).

Diastereomer 1.9.1: $^1$H NMR (400 MHz, $CDCl_3$) δ 7.62 (d, J=7.2 Hz, 2H), 7.50-7.32 (m, 8H), 7.06-6.95 (m, 1H), 6.91-6.76 (m, 2H), 6.61-6.46 (m, 1H), 5.94 (d, J=7.9 Hz, 1H), 5.64 (d, J=10.7 Hz, 1H), 5.47 (d, J=10.8 Hz, 1H), 5.36 (s, 1H), 4.60 (t, J=12.8 Hz, 2H), 3.95 (d, J=10.7 Hz, 1H), 3.71 (d, J=8.8 Hz, 1H), 3.39-3.20 (m, 2H), 2.99-2.83 (m, 1H).

After the crystallization of diastereomer 1.9.1 from a mixture of dichloromethane-hexane, the resulting crystals were analyzed using the XRD method. The obtained data (FIG. 3, Table 5) confirmed its stereochemical structure.

TABLE 5

Basic crystallographic data and refinement parameters for diastereomer 1.9.1

| Molecular formula | $C_{30}H_{25}F_2N_3O_4$ |
|---|---|
| Molecular mass | 529.53 |
| T, K | 120 |
| Crystal system | Triclinic |
| Space group | P1 |
| Z | 1 |
| a, Å | 7.2293 (7) |
| b, Å | 9.5120 (9) |
| c, Å | 10.0046 (9) |
| α, ° | 70.501 (2) |
| β, ° | 85.503 (2) |
| γ, ° | 87.171 (2) |
| V, Å$^3$ | 646.32 (11) |
| $d_{выч}$, g × cm$^{-3}$ | 1.360 |
| μ, cm$^{-1}$ | 1.01 |
| F (000) | 276 |
| $2q_{max}$, ° | 56 |
| Number of measured reflections | 7474 |
| Number of independent reflections | 6090 |
| Number of reflections c I > 2s (I) | 5042 |
| Number of refined parameters | 352 |
| R1 | 0.0459 |
| wR2 | 0.0938 |
| GOF | 1.0188 |
| Residual electron density, e × Å$^{-3}$ ($d_{max}/d_{min}$) | 0.259-0.228 |

Example 13. (12aR)-7-Hydroxy-12-[(3,4-difluorophenyl)(phenylmethyl]-3,4,12,12a-tetrahydro-1H-[1,4]oxazino[3,4-c]pyrido[2,1-f][1,2,4]triazine-6,8-dione (1.7.2) and its diastereomers 1.8.2 and 1.9.2

To a solution of 64 mg (0.12 mmol) of (12aR)-7-(benzyloxy) derivative 1.7.1, 1.8.1 or 1.91 in 3 ml of dimethylacetamide, 40 mg (0.95 mmol) of LiCl was added, and the reaction mass was heated to 80° C. and stirred for 3 hours. The reaction mass was evaporated to dryness on a rotary evaporator, the residue was purified by HPLC to give (12aR)-7-hydroxy-12-[(3,4-difluorophenyl)(phenylmethyl]-3,4,12,12a-tetrahydro-1H-[1,4]oxazino[3,4-c]pyrido[2,1-f][1,2,4]triazine-6,8-dione (1.7.2): LC MS (20 min) m/z 440 (M+1); according to $^1$H NMR data, the ratio of diastereoisomers 1.8.2 and 1.9.2 in the mixture was 1.5:1; (12aR)-7-hydroxy-12-[(10R)-(3,4-difluorophenyl)(phenylmethyl]-3,4,12,12a-tetrahydro-1H-[1,4]oxazino[3,4-c]pyrido[2,1-f][1,2,4]triazine-6,8-dione (1.8.2): LC MS (20 min), Rt=13.99 (220 nm), m/z 440 (M+1), $^1$H NMR (400 MHz, DMSO) δ 7.89-7.76 (m, 1H), 7.59-7.44 (m, 2H), 7.33-7.13 (m, 6H), 5.74 (s, 1H), 5.44 (d, J=7.6 Hz, 1H), 4.60 (d, J=7.4 Hz, 1H), 4.37 (d, J=12.7 Hz, 1H), 3.96 (d, J=8.3 Hz, 1H), 3.75-3.56 (m, 2H), 3.44-3.37 (m, 2H), 3.22-3.14 (m, 1H), and (12aR)-7-hydroxy-12-[(10S)-(3,4-difluorophenyl)(phenylmethyl]-3,4,12,12a-tetrahydro-1H-[1,4]oxazino[3,4-c]pyrido[2,1-f][1,2,4]triazine-6,8-dione (1.9.2): LC MS (20 min), Rt=14.32 (220 nm), m/z 440 (M+1), $^1$H NMR (400 MHz, DMSO) δ 7.66 (d, J=7.4 Hz, 2H), 7.46 (t, J=7.4 Hz, 3H), 7.43-7.32 (m, 2H), 7.28 (dd, J=18.9, 8.6 Hz, 1H), 7.22-7.14 (m, 1H), 5.78 (s, 1H), 5.58 (d, J=7.6 Hz, 1H), 4.52 (dd, J=10.0, 2.8 Hz, 1H), 4.37 (d, J=12.0 Hz, 1H), 3.92 (dd, J=10.8, 2.8 Hz, 1H), 3.69-3.60 (m, 2H), 3.42-3.35 (m, 1H), 3.03 (t, J=11.1 Hz, 1H).

Example 14. (12aR)-12-[(R)-(3,4-Difluorophenyl)(phenyl)methyl]-7-hydroxy-6,8-dioxo-3,4,6,8,12,12a-hexahydro-1H-[1,4]oxazino[3,4-c]pyrido[2,1-f][1,2,4]triazin-7-yl}oxy)methyl methyl carbonate (1.8.4) and (12aR)-12-[(S)-(3,4-difluorophenyl)(phenyl)methyl]-7-hydroxy-6,8-dioxo-3,4,6,8,12,12a-hexahydro-1H-[1,4]oxazino[3,4-c]pyrido[2,1-f][1,2,4]triazin-7-yl}oxy)methyl methyl carbonate (1.9.4)

The above compounds were prepared similarly to compounds 1.1.4. 1.2.4, and 1.3.4 from Example 7.

Diastereoisomer 1.8.4: LC MS (20 min), m/z 528 (M+1), $^1$H NMR (DMSO-$d_6$, 300 MHz, 80° C.) δ 7.76 (m, 1H), 7.48 (m, 2H), 7.35 (m, 1H), 7.24 (m, 5H), 5.73 (m, 1H), 5.66 (m, 3H), 4.57 (m, 1H), 4.37 (m, 1H), 4.00 (m, 1H), 3.75 (s, 3H), 3.71 (m, 1H), 3.43 (m, 1H), 3.30 (m, 1H), 3.10 (m, 1H).

Diastereoisomer 1.9.4: LC MS (20 min), m/z 528 (M+1), $^1$H NMR (DMSO-$d_6$, 300 MHz, 80° C.) δ 7.65 (m, 2H), 7.43 (m, 5H), 7.21 (m, 2H), 5.79 (d, J=8.0 Hz, 1H), 5.70 (m, 3H), 4.51 (m, 1H), 4.36 (m, 1H), 3.97 (m, 1H), 3.75 (s, 3H), 3.68 (m, 1H), 3.45 (m, 1H), 3.29 (m, 1H), 2.95 (m, 1H).

Example 15. (12aR)-7-(Benzyloxy)-12-{(3,4-difluorophenyl)[2-(methylthio)phenyl]methyl}-3,4,12,12a-tetrahydro-1H-[1,4]oxazino[3,4-c]pyrido[2,1-c][1,2,4]triazine-6,8-dione (1.10.1) and its diastereomers 1.11.1 and 1.12.1

To a mixture of 400 mg (1.222 mmol, 1 eq.) of 7-(benzyloxy)-3,4,12,12a-tetrahydro-1H-[1,4]oxazino[3,4-c]pyrido[2,1-f] [1,2,4]triazine-6,8-dione (2) and 358 mg (1.344 mmol, 1.1 eq.) of (3,4-difluorophenyl)[2-(methylthio)phenyl]methanol (6), 1166.5 mg (1.833 mmol, 1.5 eq.) of 50% $T_3R$ in ethyl acetate and 0.4 ml ethyl acetate were added. To this suspension, 235 mg (2.444 mmol, 2 eq.) of methanesulfonic acid was added, and the mixture was heated in a CEM microwave reactor for 5.5 hours at 100° C. Water (4 ml) was added to the reaction mixture while cooling with ice, and the mixture was stirred in an ice bath for 1 hour. Then, 30 ml of water was added, and the organic phase was thrice extracted with 30-ml portions of ethyl acetate. The combined organic layer was washed with a saturated $NaHCO_3$ solution, then with brine, dried over $Na_2SO_4$, and evaporated to dryness on a rotary evaporator.

Product 1.10.1 consisting of its diastereomers 1.11.1 and 1.12.1 was partially debenzylated; therefore, the mixture was used in the next stage without further purification. LC MS (3 min): Rt=1.40 (220 nm), m/z 576 (M+1).

Example 16. (12aR)-7-Hydroxy-12-{(3,4-difluoro-phenyl)[2-(methylthio)phenyl]methyl}-3,4,12,12a-tetrahydro-1H-[1,4]oxazino [3, 4-c]pyrido[2,1-e][1,2,4]triazine-6,8-dione (1.10.2) consisting of its diastereomers 1.11.2 and 1.12.2

The product prepared in Example 15 was dissolved in 10 ml of dimethylacetamide, and 259 mg (6.11 mmol, 5 eq.) of LiCl was added to this solution. The mixture was heated to 80° C. and stirred for 3 hours. The reaction mass was evaporated to dryness on a rotary evaporator, then 50 ml of 0.5M HCl was added to the remainder, the reaction mixture was stirred at room temperature for 10 min and the resulting residue was filtered off. The residue was washed with water and air-dried. The product was purified by HPLC. According to $^1$H NMR data, the product 1.10.2 (LC MS (20 min): Rt=14.49 (220 nm), m/z 486 (M+1)) consisted of diastomers 1.11.2 and 1.12.2 in the ratio 60:40.

Example 17. (12aR)-7-(Benzyloxy)-12-12-diphenyl-methyl-3,4,12,12a-tetrahydro-1H-[1,4]oxazino[3,4-c]pyrido[2,1-f][1,2,4]triazine-6,8-dione (1.13.1)

To a mixture of 380 mg (1.2 mmol) of 7-(benzyloxy)-3,4,12,12a-tetrahydro-1H-[1,4]oxazino[3,4-c]pyrido[2,1-f][1,2,4]triazine-6,8-dione (2) and 214 mg (1.2 mmol) of diphenylmethanol (7) in 7.4 g (12.0 mmol) of 50% $T_3R$ in ethyl acetate, 223 mg (2.4 mmol) of methanesulfonic acid was added, and the mixture was stirred for 16 h at 50° C. The reaction mass was cooled to room temperature, then 50 ml of ethyl acetate was added. The mixture was washed with 50 ml of saturated $NaHCO_3$ solution, dried over $Na_2SO_4$ and evaporated to dryness on a rotary evaporator. The resulting product was purified by column chromatography on silica gel with ethyl acetate. The evaporation of respective fractions yielded 407 mg (71%) of product 1.13.1: LC MS (20 min), Rt=17.10 (220 nm), m/z 494 (M+1); $^1$H NMR (400 MHz, DMSO) δ 7.66 (d, J=7.5 Hz, 2H), 7.55 (d, J=7.3 Hz, 2H), 7.45 (t, J=7.5 Hz, 2H), 7.40-7.28 (m, 5H), 7.21 (d, J=7.2 Hz, 2H), 7.19-7.09 (m, 3H), 5.66 (s, 1H), 5.57 (d, J=7.7 Hz, 1H), 5.24 (d, J=10.8 Hz, 1H), 5.05 (d, J=10.9 Hz, 1H), 4.53-4.45 (m, 1H), 4.40 (d, J=12.8 Hz, 1H), 3.92 (d, J=8.2 Hz, 1H), 3.64 (d, J=9.0 Hz, 1H), 3.45-3.37 (m, 1H), 3.23 (t, J=10.9 Hz, 1H), 2.96 (t, J=10.9 Hz, 1H).

Example 18. (12aR)-7-Hydroxy-12-diphenylmethyl-3,4,12,12a-tetrahydro-1H-[1,4]oxazino[3,4-c]pyrido[2,1-f][1,2,4]triazine-6,8-dione (1.13.2)

To a solution of 360 mg (0.73 mmol) of (12aR)-7-(benzyloxy)-12-diphenylmethyl-3,4,12,12a-tetrahydro-1H-[1,4]oxazino[3,4-c]pyrido[2,1-f][1,2,4]triazine-6,8-dione (1.13.1) in 5 ml of dimethylacetamide, 155 mg (3.65 mmol) of LiCl was added, and the reaction mass was heated to 80° C. and stirred for 3 hours. The reaction mass was then evaporated to dryness on a rotary evaporator, 50 ml of 0.5N HCl was added to the remainder, and the product was thrice extracted with 30-ml portions of EtOAc. The combined extract was washed with brine, dried over $Na_2SO_4$ and evaporated to dryness on a rotary evaporator to give 62 mg of product 1.13.2: LC MS (20 min), Rt=12.85 (220 nm), m/z 404 (M+1); $^1$H NMR (400 MHz, DMSO) δ 7.66 (d, J=7.3 Hz, 2H), 7.45 (t, J=7.3 Hz, 2H), 7.40-7.33 (m, 1H), 7.28 (s, 2H), 7.25-7.13 (m, 4H), 5.68 (s, 1H), 5.44 (d, J=7.7 Hz, 1H), 4.56 (d, J=8.0 Hz, 1H), 4.38 (d, J=13.0 Hz, 1H), 3.94 (d, J=9.1 Hz, 1H), 3.72-3.59 (m, 2H), 3.45-3.37 (m, 2H), 3.12-3.00 (m, 1H).

Example 19. ({(12aR)-12-Diphenylmethyl-3,4,12,12a-tetrahydro-1H-[1,4]oxazino[3,4-c]pyrido[2,1-f][1,2,4]triazin-7-yl}oxy)methyl methyl carbonate (1.13.4)

Prodrug 1.13.4 was prepared under conditions described in Example 7 similar to the synthesis of ({(12aR)-12-[(10S)-5,10-dihydrothieno[3,2-c][2]benzothiepin-10-yl]-4,8-di-oxo-3,4,6,8,12,12a-hexahydro-1H-[1,4]oxazino[3,4-c]pyrido[2,1-f][1,2,4]triazine-6-yl}oxy)methyl methyl carbonate (1.1.4).

Prodrug 1.13.4: LC MS (20 min), Rt=12.85 (220 nm), m/z 492 (M+1); H NMR (DMSO-$d_6$, 400 MHz) δ 7.67 (d, J=7.6 Hz, 2H), 7.46 (t, J=7.6 Hz, 2H), 7.37 (m, 2H), 7.27 (m, 2H), 7.19 (m, 3H), 5.68 (s, 1H), 5.67 (d, J=6.8 Hz, 1H), 5.63 (d, J=7.6 Hz, 1H), 5.61 (d, J=6.8 Hz, 1H), 4.51 (dd, $J_1$=10.0 Hz, $J_2$=2.8 Hz, 1H), 4.34 (d, J=13.2 Hz, 1H), 3.96 (dd, $J_1$=10.8 Hz, $J_2$=2.4 Hz, 1H), 3.72 (s, 3H), 3.68 (dd, $J_1$=11.2 Hz, $J_2$=2.8 Hz, 1H), 3.45 (t, J=10.4 Hz, 1H), 3.26 (m, 1H), 3.01 (dt, $J_1$=12.4 Hz, $J_2$=2.8 Hz, 1H).

Example 20. (12aR)-7-(Benzyloxy)-12-[bis(4-fluo-rophenyl)methyl]-3,4,12,12a-tetrahydro-1H-[1,4]oxazino[3,4-c]pyrido[2,14f][1,2,4]triazine-6,8-dione (1.14.1)

To a mixture of 0.67 g (3.1 mmol) of 7-(benzyloxy)-3,4,12,12a-tetrahydro-1H-[1,4]oxazino[3,4-c]pyrido[2,1-f][1,2,4]triazine-6,8-dione (2) and 1.0 g (3.1 mol) of bis(4-fluorophenyl)methanol (8) in 19.4 g (31.0 mmol) of 50% $T_3R$ in ethyl acetate, 0.59 g (6.2 mmol) of methanesulfonic acid was added, and the mixture was stirred for 16 h at 80° C. The reaction mass was cooled to room temperature, 150 ml of ethyl acetate was added, and the reaction mass was washed with 200 ml of saturated aqueous $NaHCO_3$ solution, dried over $Na_2SO_4$ and evaporated to dryness on a rotary evaporator. The resulting product was purified by column chromatography on silica gel with ethyl acetate. The evaporation of corresponding fractions yielded product 1.14.1: LC MS (20 min), Rt=15.66 (220 nm), m/z 530 (M=1); H NMR (400 MHz, DMSO) δ 7.76-7.67 (m, 2H), 7.55 (d, J=7.1 Hz, 2H), 7.42-7.21 (m, 8H), 6.97 (t, J=8.7 Hz, 2H), 5.76 (s, 1H), 5.65 (d, J=7.7 Hz, 1H), 5.24 (d, J=10.9 Hz, 1H), 5.06 (d, J=10.8 Hz, 1H), 4.47 (d, J=7.2 Hz, 1H), 4.40 (d, J=12.6 Hz, 1H), 3.91 (d, J=8.3 Hz, 1H), 3.64 (d, J=9.0 Hz, 1H), 3.42 (t, J=10.5 Hz, 1H), 3.23 (t, J=10.8 Hz, 1H), 3.01 (t, J=11.4 Hz, 1H).

Example 21. (12aR)-12-[Bis(4-fluorophenyl)methyl]-7-hydroxy-3,4,12,12a-tetrahydro-1H-[1,4]oxazino[3,4-c]pyrido[2,1-][1,2,4]triazine-6,8-dione (1.14.2)

Product 1.14.2: LC MS (20 min), Rt=12.72 (220 nm), m/z 440; $^1$H NMR (400 MHz, DMSO) δ 11.61 (br.s, 1H), 7.76-7.64 (m, 2H), 7.39-7.18 (m, 5H), 7.03 (t, J=8.7 Hz, 2H), 5.77 (d, J=11.9 Hz, 1H), 5.52 (d, J=7.6 Hz, 1H), 4.63-4.46 (m, 1H), 4.37 (d, J=13.4 Hz, 1H), 3.92 (d, J=8.1 Hz, 1H), 3.72-3.57 (m, 2H), 3.39 (t, J=10.8 Hz, 1H), 3.11 (t, J=11.1 Hz, 1H) was prepared under conditions described in Example 17 for the synthesis of compound 1.13.2.

Example 22. ({(12aR)-12-[Bis(4-fluorophenyl)) methyl]-3,4,12,12a-tetrahydro-1H-[1,4]oxazino[3,4-c]pyrido[2,1-][1,2,4]triazin-7-yl}oxy)methyl methyl carbonate (1.14.4)

Prodrug 1.14.4 was prepared under conditions described in Example 7 for the synthesis of ({(12aR)-12-[(10S)-5,10-dihydrothieno[3,2-c][2]benzothiepin-10-yl]-4,8-dioxo-3,4,6,8,12, 12a-hexahydro-1H-[1,4]oxazino[3,4-c]pyrido[2,1-f][1,2,4]triazine-6-yl}oxy)methyl methyl carbonate (1.1.4).

Prodrug 1.14.4: LC MS (20 min), Rt=12.85 (220 nm), m/z 528 (M+1); H NMR (DMSO-$d_6$, 400 MHz) δ 7.73 (m, 2H), 7.39 (d, J=7.6 Hz, 1H), 7.27-7.32 (m, 4H), 7.02 (m, 2H), 5.78 (s, 1H), 5.71 (d, J=7.6 Hz, 1H), 5.68 (d, J=6.8 Hz, 1H), 5.61 (d, J=6.8 Hz, 1H), 4.50 (dd, $J_1$=10.0 Hz, $J_2$=3.2 Hz, 1H), 4.33 (d, J=13.2 Hz, 1H), 3.95 (dd, $J_1$=10.8 Hz, $J_2$=2.8 Hz, 1H), 3.72 (s, 3H), 3.68 (dd, $J_1$=11.2 Hz, $J_2$=3.2 Hz, 1H), 3.46 (t, J=10.4 Hz, 1H), 3.26 (dt, $J_1$=11.6 Hz, $J_2$=2.0 Hz, 1H), 3.05 (dt, $J_1$=12.4 Hz, $J_2$=3.2 Hz, 1H).

Example 23. Evaluation of In Vitro Activity of Novel Inhibitors Against Influenza Virus Isolates in MDCK Cell Culture Using an Enzyme Immunoassay (EIA) Procedure.

Protocol 1 of ImQuest BioSciences (Frederick, Maryland, USA) was used to determine the activity of the compounds of influenza a/California/2009 (H1N1) isolates.

Preparation of cells. MDCK cells (dog kidney cells, CCL-34) were obtained from ATCC and passaged in DMEM with the addition of 10% FBS, 2 mM of L-glutamine, 100 U/ml of penicillin, 100 μg/ml of streptomycin, 1 mM of sodium pyruvate, and 0.1 mM of NEAA, and a T-75 flask before use in antiviral analysis. On the day preceding the analysis, the cells were separated 1:2 to ensure that in the process of infecting them they were in an exponential growth phase. Determination of the number of cells and their viability was performed using a hemocytometer and elimination of the dye with trypan blue. The cell viability was more than 95% for the cells to be used in the analysis. The cells were resuspended at 1×104 cells per well in a tissue culture medium and added into flat-bottom microtiter plates in a volume of 100 μl. The plates were incubated overnight at 37° C./5% $CO_2$ to enable cell adhesion.

Preparation of the virus. The virus of influenza A/CA/04/09 (NR-13685-) was obtained from BEI Resources (Manassas, VA) and grown in MDCK cells to produce pools of source viruses. The pre-titrated virus aliquot was removed from the freezer (−80° C.) and allowed to thaw slowly to room temperature in a biosafety cabinet. The virus was resuspended and diluted in an assay medium (DMEM plus 2 mM of L-glutamine, 100 E/ml of penicillin, 100 μg/ml of streptomycin, 1 mM of sodium pyruvate, 0.1 mM of NEAA, and 1 μg/ml of TPCK-treated trypsin) in such a way that the amount of virus to be added in each 100-μl well was determined to kill from 85 to 95% of cells 4 days after infection (MOI 0.01).

Plate format. Each plate contained wells for cell control (cells only), wells for virus control (cells plus virus), wells for colorimetric drug control (medicine only), and experimental wells (medicine plus cells plus virus). The samples were tested three times for effectiveness with five half dilutions per compound.

XTT efficacy and toxicity. Following incubation at 37° C. in a 5% $CO_2$ incubator, test plates were stained with XTT (2,3-bis(2-methoxy-4-nitro-5-sulfophenyl)-5-[(phenylamino)carbonyl]-2H-tetrazolium hydroxide, Sigma-Aldrich) tetrazolium dye. XTT-tetrazolium is metabolized by mitochondrial enzymes of metabolically active cells to a soluble product formazan, which allows rapid quantitative analysis of inhibition of virus-induced cell destruction by antiviral test substances. An XTT solution was prepared daily as a stock of 1 mg/ml in RPMI1640. A solution of phenazine metasulfate (PMS, Sigma-Aldrich) was prepared at a concentration of 0.15 mg/ml in PBS and stored in the dark at −20° C. The XTT/PMS source material was prepared immediately before use by adding 40 μl of PMS per ml of XTT solution. Fifty microliters of XTT/PMS were added to each well, and the plate was reincubated for 4 hours at 37° C. The plates were hermetically sealed with adhesive plate sealers and gently shaken or turned over several times to mix the soluble product formazan, and the plate was read spectrophotometrically at 450/650 nm using a Molecular Devices Vmax microplate reader.

Data analysis. The raw data was collected from the Softmax Pro software and imported into a Microsoft Excel XLfit4 spreadsheet for analysis by calculation of four conformity parameters.

Protocol 2 of Mechnikov Research Institute of Vaccines and Sera (Mechnikov NIIVS, Moscow) was applied to determine the activity of the compounds of influenza isolates A/Aichi/2/69 (H3N2) and A/Perth/265/2009 (H1N1pdm09) (H275Y).

To determine the anti-influenza activity of the novel inhibitors (J and the prototype, MDCK cells were planted in Costar 96-well plates with a mean density of 30000-35000 cells per well and grown in Eagle's Minimum Essential Medium (EMEM) in the presence of 5% fetal calf serum and 10 mM of glutamine as a complete monolayer. Prior to infection with the virus, the cells were twice washed with serum-free medium. Test compounds were added to the cells in a 2-fold concentration in 100 μl of EMEM. The same medium was added in the virus control (100 μl) and in the cell control (200 μl). Since we used human influenza virus strains, the test samples and virus dilutions were prepared on a medium with the addition of 2.5 μg/ml of TRNC trypsin. After a 2-hour incubation of cells with test drugs at 37° C., 100 μl of allantoic virus diluted on a medium with 5 μg/ml of TRNC trypsin (from 0.1 to 5 PFU per cell) was added into wells, except for cell control. The plates were then incubated for 24 hours at 37° C. in 5% $CO_2$. After incubation, the medium was removed and the cells were fixed with 80% acetone on a phosphate-buffer saline (PBS) for 20 minutes, well-dried, and washed 3 times with PBS combined with 0.05% Tween 20 (EIA solution). Said solution was used in all subsequent washing procedures. Then, 100 μl of PBS solution with 1% fetal serum and 0.05% Tween 20 were added, and the cells were incubated for 30 minutes at 37° C. After removal of the solution, 100 μl of monoclonal antibodies (MCAS) to the internal proteins of the influenza A virus (NP+M1) diluted 1:1000 in the EIA solution were added to the cells. After incubation with antibodies for 1 hour at 37° C. and subsequent 3-fold washing, 100 μl of rabbit IgG against mouse IgG labeled with horseradish peroxidase in a 1:5000 dilution was added into the wells, and the cells were incubated for another 1 hour at 37° C. After 4-fold washing, the bound peroxidase was revealed by addition of a 100 μl of 0.05% solution of o-phenylenediamine to the wells in a 0.003% citrate pH 5.0 buffer containing 0.003% $H_2O_2$. The plates were kept for 15-30 minutes in the dark until the color appeared, the reaction was stopped by adding 50 μl of 4N $H_2SO_4$, and optical density (OD) was measured on an automatic spectrophotometer at a wavelength of 450 nm. For a cell control, virus-uninfected wells were used. The percentage of viral reproduction inhibition by the test compound was found by the formula: the percentage of inhibition=100−(OD of experiment−OD of cell control/OD of viral control in the absence of a compound−OD of cell control). For one point of the experiment, four plate wells were used, each value representing the arithmetic mean calculated from this experiment. The concentration of drug that reduces the OD value by 50% was taken as an inhibitory concentration of 50 ($IC_{50}$). Antiviral activities of novel inhibitors and Baloxavir in influenza A virus isolates in MDCK cell culture are presented in Table 3.

Example 24. Pharmaceutical Compositions in Tablets

Starch (1700 mg), ground lactose (1700 mg), talc (400 mg), and 1200 mg of a prodrug 1.1.4, or 1.11.4, or 1.14.4 were mixed and pressed into a bar. The resulting bar was crushed into granules and sifted through a sieve to collect granules of 14-16 mesh size. The granules obtained in this way were formed into tablets of a suitable shape weighing 80 or 160 mg each.

Example 25. Pharmaceutical Composition in Capsules

A prodrug of formula 1.1.4 or 1.11.4 or 1.14.4 was thoroughly mixed with lactose powder in the ratio 2:1. The resulting powder mixture was packed in gelatin capsules of suitable size, 36 or 72 mg in each capsule.

INDUSTRIAL APPLICABILITY

This invention can be used in medicine and veterinary.

The invention claimed is:

1. A compound selected from the group consisting of:

a (12aR)-12-(6,7-difluoro-5,10-dihydrothieno[3,2-c][2] benzothiepin-10-yl)-3,4,12,12a-tetrahydro-1H-[1,4] oxazino[3,4-c]pyrido[2,1-f][1,2,4]triazine-6,8-dione of formula 1.1, a (12aR)-12-[(10S)-6,7-difluoro-5,10-dihydrothieno[3,2-c][2]benzothiepin-10-yl]-3,4,12,12a-tetrahydro-1H-[1, 4]oxazino [3,4-c]pyrido[2,1-f][1,2,4]triazine-6,8-dione of formula 1.2, and a (12aR)-12-[(10R)-6,7-difluoro-5,10-dihydrothieno[3,2-c][2]benzothiepin-10-yl]-3,4,12,12a-tetrahydro-1H-[1, 4] oxazino[3,4-c]pyrido[2,1-f][1,2,4]triazine-6,8-dione of formula 1.3, 1.1

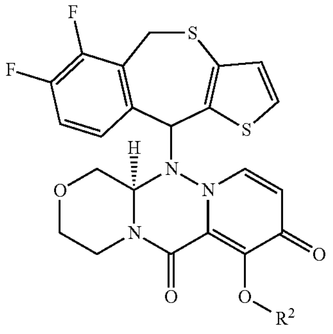

-continued 1.2

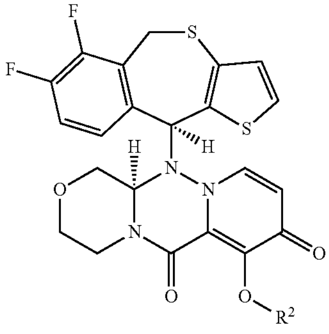

1.3

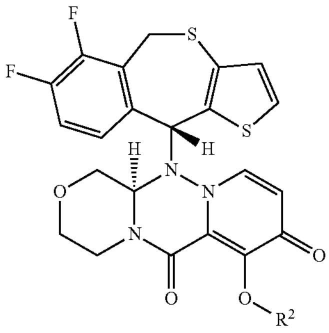

wherein $R^2$ is hydrogen or {[($C_1$-$C_3$alkyl)oxycarbonyl]-oxy}methoxy, and stereoisomers thereof.

2. The compound of claim 1, wherein the compound is selected from the group consisting of:

(12aR)-7-hydroxy-12-(6,7-difluoro-5,10-dihydrothieno [3,2-c][2]benzothiepin-10-yl)-3,4,12, 12a-tetrahydro-1H-[1,4]oxazino[3,4-c]pyrido[2,1-f][1,2,4]triazine-6, 8-dione (1.1.2), (12aR)-7-hydroxy-12-[(10S)-6,7-difluoro-5,10-dihydrothieno[3,2-c][2]benzothiepin-10-yl]-3,4,12,12a-tetrahydro-1H-[1,4]oxazino[3,4-c]pyrido[2,1-f][1,2,4]triazine-6,8-dione (1.2.2), (12aR)-7-hydroxy-12-[(10R)-6,7-difluoro-5,10-dihydrothieno[3,2-c][2]benzothiepin-10-yl]-3,4,12,12a-tetrahydro-1H-[1,4]oxazino[3,4-c]pyrido[2,1-f][1,2,4]triazine-6,8-dione (1.3.2), {[(12aR)-12-(6,7-difluoro-5,10-dihydrothieno[3,2-c][2] benzothiepin-10-yl)-6,8-dioxo-3,4,12,12a-tetrahydro-1H-[1,4]oxazino[3,4-c]pyrido[2,1-f][1,2,4]triazin-7-yl]oxy}methyl methyl carbonate (1.1.4), ({(12aR)-12-[(10S)-6,7-difluoro-5,10-dihydrothieno[3,2-c][2]benzothiepin-10-yl]-6,8-dioxo-3,4,12, 12a-tetrahydro-1H-[1,4]oxazino[3,4-c]pyrido[2,1-f][1,2,4]triazin-7-yl}oxy)methyl methyl carbonate (1.2.4), and ({(12aR)-12-[(10R)-6,7-difluoro-5,10-dihydrothieno[3,2-c][2]benzothiepin-10-yl]-6,8-dioxo-3,4,12, 12a-tetrahydro-1H-[1,4]oxazino[3,4-c]pyrido[2,1-f][1,2,4]triazin-7-yl}oxy)methyl methyl carbonate (1.3.4)

1.1.2
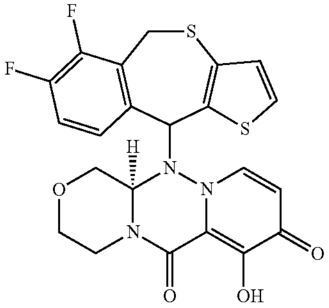
1.2.2
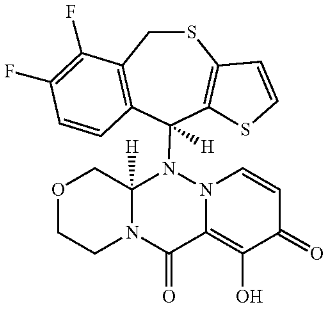
1.3.2
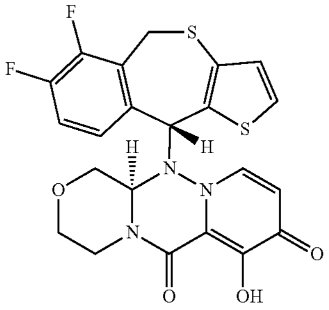
1.1.4
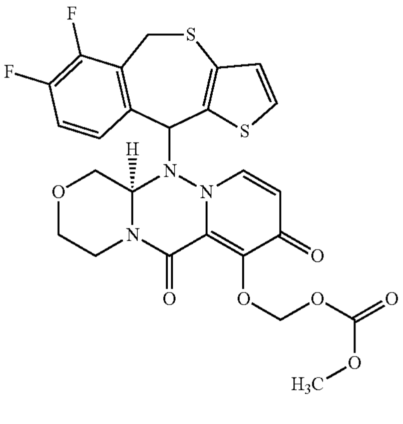
-continued
1.2.4
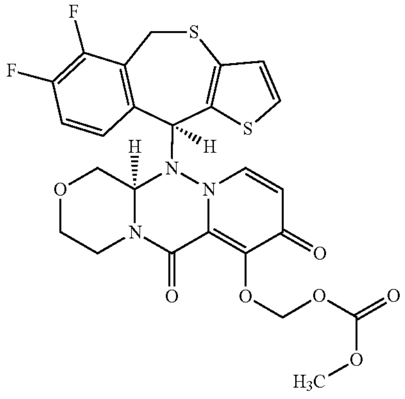
1.3.4
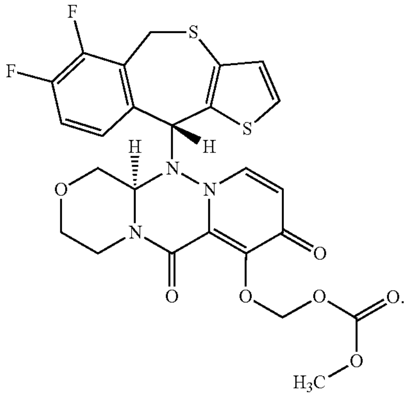
3. The compound of claim 2, wherein the compound is ({(12aR)-12-[(10R)-6,7-difluoro-5,10-dihydrothieno[3,2-c][2]benzothiepin-10-yl]-6,8-dioxo-3,4,12,12a-tetrahydro-1H-[1,4]oxazino[3,4-c]pyrido[2,1-f][1,2,4]triazin-7-yl}oxy)methyl methyl carbonate (1.3.4)
1.3.4
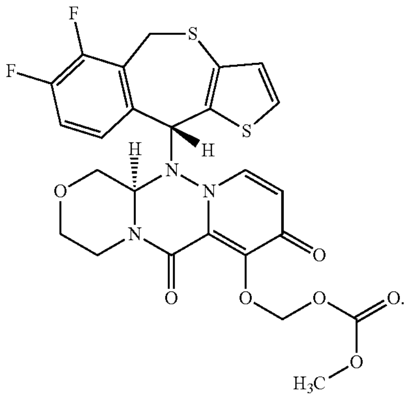
4. The compound of claim 2, wherein the compound is (12aR)-7-hydroxy-12-[(10R)-6,7-difluoro-5,10-dihydrothieno[3,2-c][2]benzothiepin-10-yl]-3,4,12,12a-tetrahydro-1H-[1,4]oxazino[3,4-c]pyrido[2,1-f][1,2,4]triazine-6,8-dione (1.3.2)

1.3.2
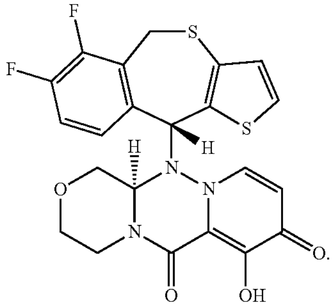
* * * * *